US008053406B2

(12) United States Patent
Kachlany

(10) Patent No.: US 8,053,406 B2
(45) Date of Patent: Nov. 8, 2011

(54) COMPOSITIONS FOR THE TREATMENT OF CANCER, AND METHODS FOR TESTING AND USING THE SAME

(75) Inventor: Scott Charles Kachlany, Bridgewater, NJ (US)

(73) Assignee: University of Medicine and Dentistry of New Jersey, Somerset, NJ (US)

( * ) Notice: Subject to any disclaimer, the term of this patent is extended or adjusted under 35 U.S.C. 154(b) by 160 days.

(21) Appl. No.: 12/154,843

(22) Filed: May 27, 2008

(65) Prior Publication Data

US 2009/0075883 A1    Mar. 19, 2009

Related U.S. Application Data

(63) Continuation-in-part of application No. PCT/US2006/045258, filed on Nov. 25, 2006, application No. 12/154,843, which is a continuation-in-part of application No. 12/150,038, filed on Apr. 23, 2008, now abandoned.

(60) Provisional application No. 60/739,537, filed on Nov. 25, 2005, provisional application No. 60/925,794, filed on Apr. 23, 2007.

(51) Int. Cl.
  *A01N 37/18* (2006.01)
(52) U.S. Cl. ........................................ 514/1.1; 530/350
(58) Field of Classification Search ........................ None
  See application file for complete search history.

(56) References Cited

FOREIGN PATENT DOCUMENTS

WO    WO 97/16531    5/1997

OTHER PUBLICATIONS

Diaz et al, Microbial Pathogenesis, published Jan 2006, 40:48-55.*
Kaplan et al, J Clin Microbiol, 2002, 40:1181-1187.*
Pasechnik, Exp Opin Invest, Drugs, 2000, 9:1243-1256.*
Tomkinson et al, Leuk Res, 2003, 27:1039-1050.*
Tsai et al., Extraction and Isolation of a Leukotoxin from *Actinobacillus actinomycetemcomitans* with Polymyxin B, Infection and Immunity, 43:700-705 (1984).
Simpson et al., Killing of Human Myelomonocytic Leukemia and Lymphocytic Cell Lines by *Actinobacillus actinomycetemcomitans* Leukotoxin, Infection and Immunity, 56:1162-1166 (1988).
Fukunaga et al., *Actinobacillus actinomycetemcomitans* induces lethal effects on the macrophage-like human cell line U937, 16:284-289 (2001).
Balashova et al., "Leukotoxin confers beta-hemolytic activity to *Actinobacillus actinomycetemcomitans*", Infection and Immunity, 74(4):2015-2021, 2006.
DiRienzo et al., "Monoclonal antibodies to leukotoxin of *Actinobacillus actinomycetemcomitans*", Infection and Immunity, 47(1):31-36, 1985.
Hormozi et al., "Target cell specificity of the *Pasteurella haemolytica* leukotoxin is unaffected by the nature of the fatty-acyl group used to activate the toxin in vitro", FEMS Microbiology Letters, 169:139-145, 1998.
Lally et al., "RTX toxins recognize a β2 integrin on the surface of human target cells", The Journal of Biological Chemistry, 272(48):30463-30469, 1997.
Linhartová et al., "RTX proteins: a highly diverse family secreted by a common mechanism", FEMS Microbiol Rev, 1-37, 2010 (E pub ahead of print).
Ohta et al., "Nuclease-sensitive binding of an *Actinobacillus actinomycetemcomitans* leukotoxin to the bacterial cell surface", Infection and Immunity, 59(12):4599-4605, 1991.
Taichman et al., Biochemical and morphological characterization of the killing of human monocytes by a leukotoxin derived from *Actinobacillus actinomycetemcomitans*, Infection and Immunity, 28(1):258-268, 1980.
Thumbikat et al., "Biological effects of two genetically defined leukotoxin mutants of *Mannheimia haemolytica*", Microbial Pathogenesis 34:217-226; 2003.
Spitznagel et al., "Regulation of leukotoxin in leukotoxic and nonleukotoxic strains of *Actinobacillus actinomycetemcomitans*", Infection and Immunity, 59(4):1394-1401, 1991.

* cited by examiner

*Primary Examiner* — Misook Yu
*Assistant Examiner* — Mark Halvorson
(74) *Attorney, Agent, or Firm* — Fox Rothschild LLP

(57) ABSTRACT

A composition comprising leukotoxin proteins isolated from a bacterium is provided. In this composition, greater than 85% of the leukotoxin proteins are chemically modified at a basic amino acid residue, and the proteins induce cell death in myeloid leukocytes, while remaining substantially non-toxic to lymphoid leukocytes, lymphocytes, and red blood cells. Also provided is a method of selectively inducing cell death in myeloid leukocytes. The method comprises contacting the myeloid leukocytes with a composition comprising leukotoxin proteins. These leukotoxin proteins may be isolated from the NJ4500 strain of Actinobacillus actinomycetemcomitans. A method of purifying leukotoxin protein from the NJ4500 strain of Actinobacillus actinomycetemcomitans is also provided, as well as an assay that allows for the rapid determination of the activity of a given drug against leukemic cells either taken from a patient or derived from a cell line. The assay is performed in the presence of whole blood or serum.

3 Claims, 10 Drawing Sheets

FIG. 1

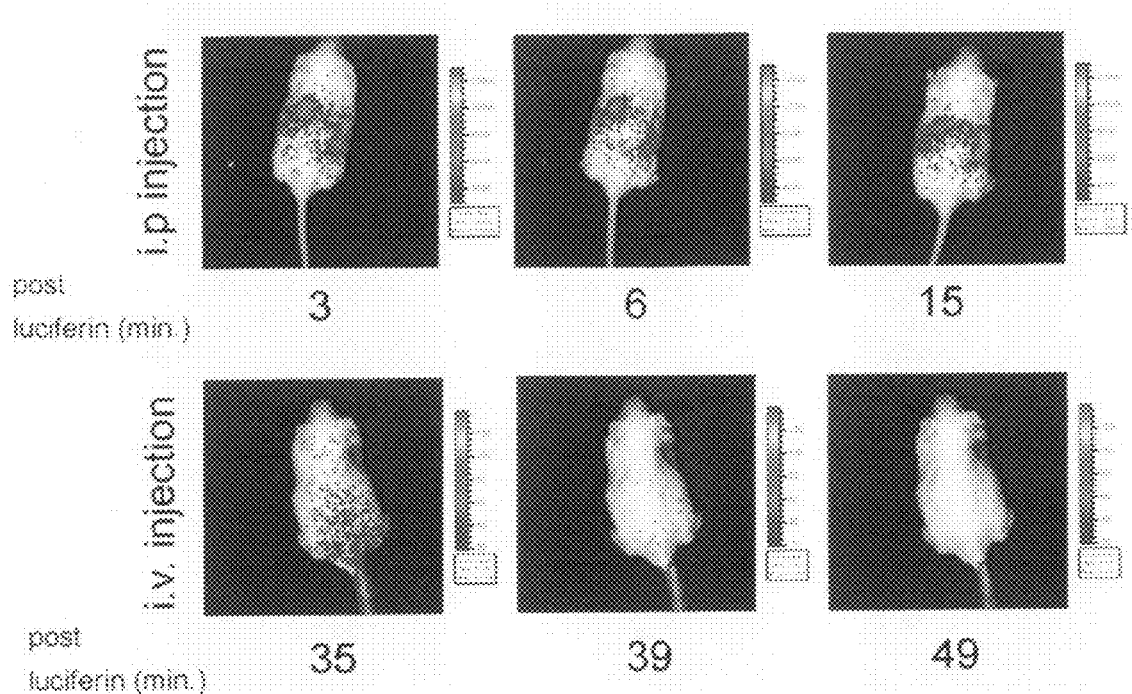

COMPOSITIONS FOR THE TREATMENT OF CANCER, AND METHODS FOR TESTING AND USING THE SAME

CROSS REFERENCE TO RELATED APPLICATIONS

The present application is a Continuation In Part of PCT Application No. PCT/US2006/045258, filed Nov. 25, 2006, which, in turn, claims priority under 35 U.S.C. §119(e) from U.S. Provisional Application Ser. No. 60/739,537, filed Nov. 25, 2005; and U.S. Non-Provisional application Ser. No. 12/150,038, filed Apr. 23, 2008, which, in turn, claims priority under 35 U.S.C.§119(e) from U.S. Provisional Application Ser. No. 60/925,794, filed Apr. 25, 2007. The entire contents of all prior listed applications are incorporated by reference herein.

RELATED FEDERALLY SPONSORED RESEARCH

The work described in this application was sponsored at least in part, under Grant No. R01 DE16133, from the National Institute of Dental and Craniofacial Research, and under Grant No. NIH R01DE16133, from the National Institutes of Health. Accordingly, the Government has certain rights in the invention.

FIELD OF THE INVENTION

The present invention is generally related to agents and compositions that demonstrate the ability to treat certain cancers, and to a method and system for the testing of such agents and compositions under physiological conditions. More particularly, the agents and compositions comprise a repeat in toxin (RTX) molecule that demonstrates leukocyte specificity, and that specifically targets myeloid leukocyte cells, as well as to an assay that allows for the rapid determination of the activity of a given drug against cancer cells, such as leukemic cells, either taken from a patient or derived from a cell line.

BACKGROUND OF THE INVENTION

Bacteria and their toxins have been investigated for their anticancer activities. In the 1970s, bacteria (such as non-pathogenic *Clostridium*) were used for the treatment of malignant brain tumors, but the tumors recurred in these brain tumor patients. More than 100 microorganisms have been studied for their potential anticancer activities, and many bacteria have growth specificity for tumors that is 1000 times greater than for other tissue.

While their anti-tumor activities make many bacteria attractive therapeutic agents, there are inherent risks to administering live bacteria to humans. A safer and more effective strategy has been to use biological toxins, specifically from bacteria, as therapeutic agents. Bacterial toxins are not only toxic, but are also highly specific for certain cell types, or can be engineered to be specific by fusing the toxin to other molecules. Many bacterial toxins are able to enter mammalian cells where they exert their toxic effects. Because of extensive evolutionary adaptation between bacteria and their hosts, bacteria have become very good at "developing" highly effective toxins.

Each year, more than 60,500 people die of hematologic malignancies (leukemia, lymphoma, myeloma) with more than 110,000 new annual diagnoses in the US alone. Current treatment for these cancers includes the use of synthetic compounds that target the cell division process of nearly all cells of the body, not just the cancerous ones. As a result, devastating side effects are all too common. Furthermore, a significant percentage of patients eventually show resistance to many of the drugs, thus rendering treatment largely ineffective. Indeed, there is an effort to identify agents that induce cancer cell death by methods other than damage to DNA or cell division.

While the drugs currently in use are toxic for cells, they are not highly specific. A new class of therapeutic agents for the treatment of hematologic malignancies, and cancer in general, includes drugs that exhibit specificity for predominantly the cancerous cell type. Examples of targeted therapeutics include Rituximab, which is a monoclonal antibody against B-lymphocytes, and Mylotarg, an antibody-anti-tumor antibiotic fusion directed against cells of myelomonocytic lineage.

*Actinobacillus actinomycetemcomitans* is a Gram negative pathogen that inhabits the oral cavities of humans. *A. actinomycetemcomitans* is the etiologic agent of localized aggressive periodontitis (LAP), a rapidly progressing and destructive disease of the gingiva and periodontal ligaments. Among its many virulence factors, *A. actinomycetemcomitans* produces an RTX (repeats in toxin) leukotoxin. *A. actinomycetemcomitans* leukotoxin is an approximately 115 kDa protein that kills specifically leukocytes of humans and Old World Primates. Leukotoxin is part of the RTX family that includes *E. Coli* α-hemolysin (HlyA) and Bordetella pertussis adenylate cyclase (CyaA). Leukotoxin may play an important role in *A. actinomycetemcomitans* pathogenesis by helping the bacterium destroy gingival crevice polymorphonuclear leukocytes (PMNs) and monocytes, resulting in the suppression of local immune defenses.

The initial identification and testing of novel anti-cancer agents relies on in vitro killing assays using relevant cancer cell lines. While in vitro assays performed under cell culture conditions prove useful and necessary for preclinical testing of new therapeutics, extrapolation to the physiological conditions of a living organism is often difficult or impossible (27). Because of the high cost of drug development ($800 million), new drug screens are constantly being sought to more efficiently eliminate or identify candidate therapeutic agents (27). Indeed, increasing the clinical success rate from ⅕ to ⅓ because of more effective preclinical drug screens would reduce drug development costs by more than $200 million (27).

The activity, specificity, or toxicity of a compound in the physiological environment can vary significantly from cell culture conditions. While no in vitro assay or screen can represent the complexity of the human body, several assays have been developed to more closely mimic in vivo conditions. Several of these assays include the colony forming cell assay using bone marrow cells (27,29), hepatic drug biotransformation assays (3), and assays in whole blood (4,45). Because most chemotherapeutic agents are administered intravenously and are therefore immediately affected by blood cell components, screening for potential drugs in the presence of whole blood would be expected to yield more meaningful results. Blood contains biological components, such as proteases, antibody, and blood cells, which can affect the nature of a compound. For example, red blood cells and plasma proteins are known to affect the pharmacokinetics of drugs such as the anti-cancer agents docetaxel and gemcitabine (8,9). Vaidyanathan et al. (43) also reported that the cardioprotective drug, dexrazoxane, inhibits binding of the anti-cancer agent, doxorubicin, to red blood cells and that this interaction alters the pharmacokinetics of doxorubicin, and Clarke et al. (4) used an in vitro whole blood assay to study the binding affinity of a surrogate anti-CD11a monoclonal antibody to blood components. In addition, leukocytes produce a cytochrome P450 isoform (CYP2E1) that is involved in drug biotransformation (3). Thus, identifying and studying drugs in the presence of whole blood or blood components can offer a unique advantage over assays using cells in monoculture.

For studies on leukemia therapeutics, the cell line HL-60 is used as a standard target cell line. HL-60 cells were originally isolated from a 36-year-old female patient with acute promyelocytic leukemia (13). Testing the efficacy of anti-leukemia therapeutics against HL-60 cells in whole blood or other biological material is currently a challenge due to the inefficiency in differentiating the viability of HL-60 cells from other cells.

Thus, there remains a need for the identification and development of therapeutic agents and strategies, for the treatment of cancers such as leukemia, and for the development of effective testing methodology, such as efficient screens for therapeutics such as anti-leukemia agents, and particularly, for the facilitation of preclinical studies on a highly specific bacterial leukotoxin as a novel anti-leukemia therapeutic agent.

SUMMARY OF THE INVENTION

Accordingly, in a first embodiment of the invention, a composition for the treatment cancers, and particularly, hematologically related cancers, is disclosed that comprises leukotoxin proteins isolated from a bacterium. In this composition, greater than 85% of the leukotoxin proteins are chemically modified at a basic amino acid residue, and the proteins induce cell death in myeloid leukocytes, while remaining substantially non-toxic to lymphoid leukocytes, lymphocytes, and red blood cells.

Also, in a method of treatment aspect, there is provided a method of selectively inducing cell death in myeloid leukocytes. The method comprises contacting the myeloid leukocytes with a composition comprising leukotoxin proteins. These leukotoxin proteins may be isolated from the NJ4500 strain of *Actinobacillus actinomycetemcomitans*. A method of purifying leukotoxin protein from the NJ4500 strain of *Actinobacillus actinomycetemcomitans* is also provided.

Accordingly, in a second embodiment of the invention, a stable bioluminescent HL-60 cell line whose viability can be rapidly and effectively determined in the presence of whole blood and live animals has now been developed along with an assay that allows for the rapid determination of the activity of a given drug against a cell sample, such as leukemic cells, either taken from a patient or derived from a cell line. The assay is carried out in the presence of whole blood or serum. This quantitative assay can screen thousands of drugs at a time or multiple concentrations of a drug in a 96- or 384-well format.

The present assay uses HL-60 cells that have been engineered that stably express firefly luciferase and produce light, whereby such bioluminescent HL-60luc cells may be rapidly detected in whole blood, eg. with a sensitivity of approximately 1000 viable cells. As demonstrated herein, treatment of HL-60luc cells with a bacterial leukocyte-specific toxin or the drug chlorambucil reveals that the bioluminescent viability assay is more sensitive than the trypan blue dye exclusion assay. HL-60luc cells administered intraperitoneally (i.p) or intravenously (i.v.) were visualized in living mice using an in vivo imaging system (IVIS). The rapidity and ease of detecting HL-60luc cells in biological fluid indicates that this cell line can be used in high throughput screens for the identification of drugs with anti-leukemia activity under physiological conditions.

Accordingly, it is a principal object of the invention to provide a series of modified leukotoxin proteins, and compositions comprising them, that can be used for the treatment of cancers, ad particularly, cancers that are hematologically related.

It is a further object of the invention to provide a method for the preparation of the modified leukotoxin proteins by their isolation and purification from a bacterium, eg. from the NJ4500 strain of *Actinobacillus actinomycetemcomitans*.

It is a yet further principal object of the invention to provide a an assay and associated methodology, for the testing of candidate therapeutic agents for the treatment of cancers, that is rapid and efficient, and that can assess the activity of the candidate agents under physiological conditions.

A still further object of this invention is to provide methods of treating cancers and conditions by the administration of the leukotoxin proteins and compositions comprising them.

Other important objects and features of the invention will be apparent from the following description of the invention taken in connection with the accompanying drawings in which:

BRIEF DESCRIPTION OF THE DRAWINGS

FIG. 1 shows fluorescence microscopy images of leukemia HL-60 cells when exposed to LtxA.

FIG. 12 shows bioluminescent imaging of HL-60luc cells in living mice. Swiss-Webster mice were anesthesized with XXX and injected with 106 HL-60luc cells intraperitoneally (i.p.; top) or intravenously (i.v.; bottom) and followed by luciferin i.p. Mice were imaged with the IVIS 50 instrument at different times post luciferin injection. The scale on the right of each image indicates surface radiance (photons/second/$cm^2$/steradian).

DETAILED DESCRIPTION OF THE INVENTION

Figure 1:
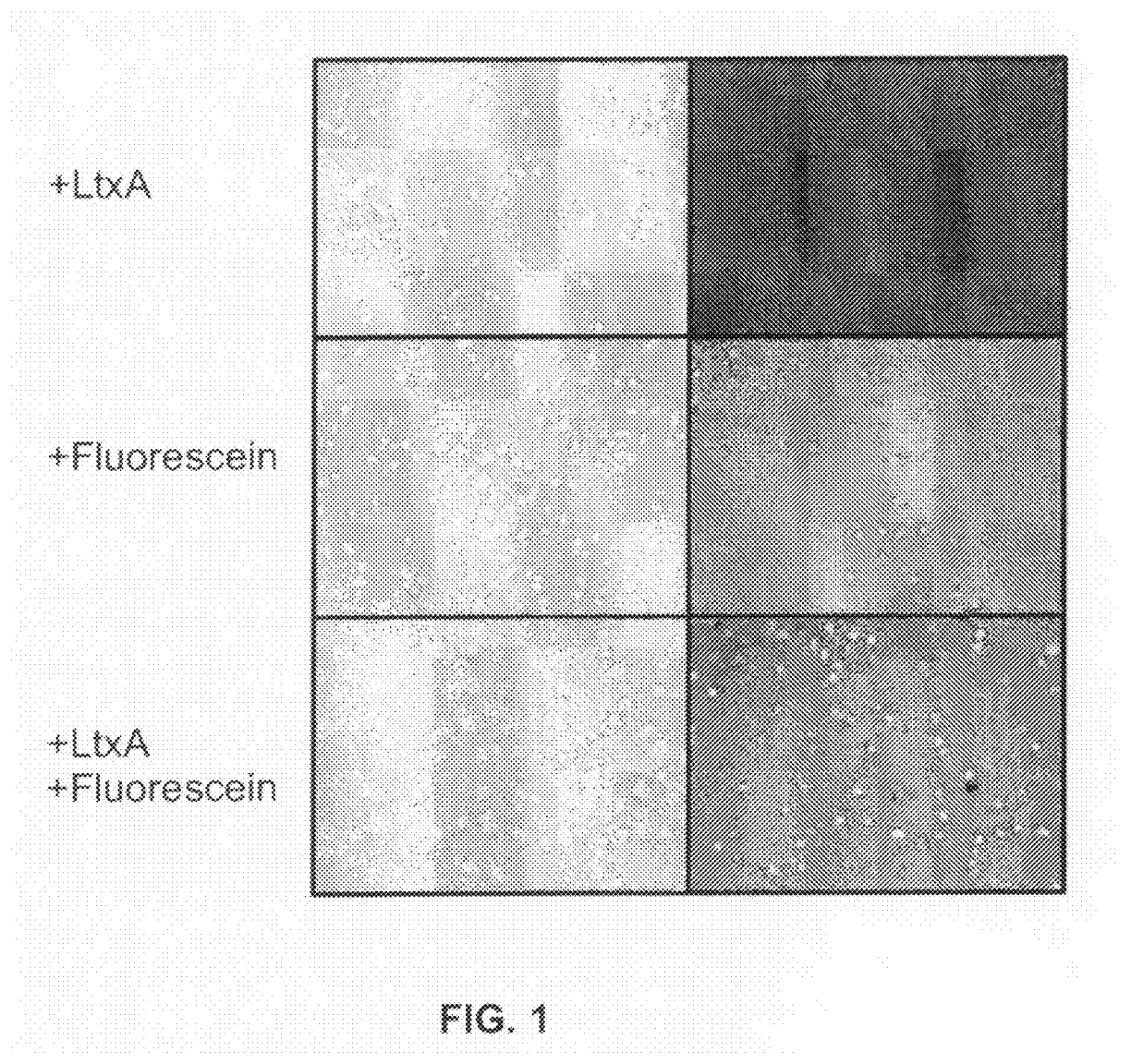

Leukotoxin is an effective cell-delivery protein, permeating leukemia cells and penetrating to the inside of specific cells. Leukotoxin mediated cell-delivery is demonstrated by introducing fluorescing molecules to specific cells, and measuring cell-delivery by monitoring the fluorescence by fluorescent microscopy. As shown in FIG. 1, the leukotoxin LtxA facilitates delivery of fluorescein into HL-60 leukemia cells. The leukotoxin forms pores or disruptions in the host cell membranes, and these openings in the membrane may allow the passage and entry of small molecules. In FIG. 1, HL-60 cells were treated with fluorescein, a reagent that can be easily tracked by fluorescence microscopy. Fluorescein exhibits a green fluorescence color under the microscope, and is approximately the same molecular weight as many of the cancer drugs currently in use. The cells treated with leukotoxin (LtxA) and fluorescein (FIG. 1, bottom panel) exhibited more intense and abundant fluorescence than the cells treated with fluorescein alone (FIG. 1, center panel), indicating that leukotoxin is able to increase the number of fluorescein molecules that enter the cells.

Not only is leukotoxin capable of penetrating cells, but this penetration is toxic and lethal to HL-60 cells. HL-60 cells were modified to express luciferase genes, and with this HL-60luc system, it was shown that at certain concentrations, leukotoxin is quite toxic to the HL-60luc cells. By monitoring the luminescence of the cells, nearly 80% of the cells were killed by concentrations of leukotoxin as low as 200 ng/ml.

Figure 2:
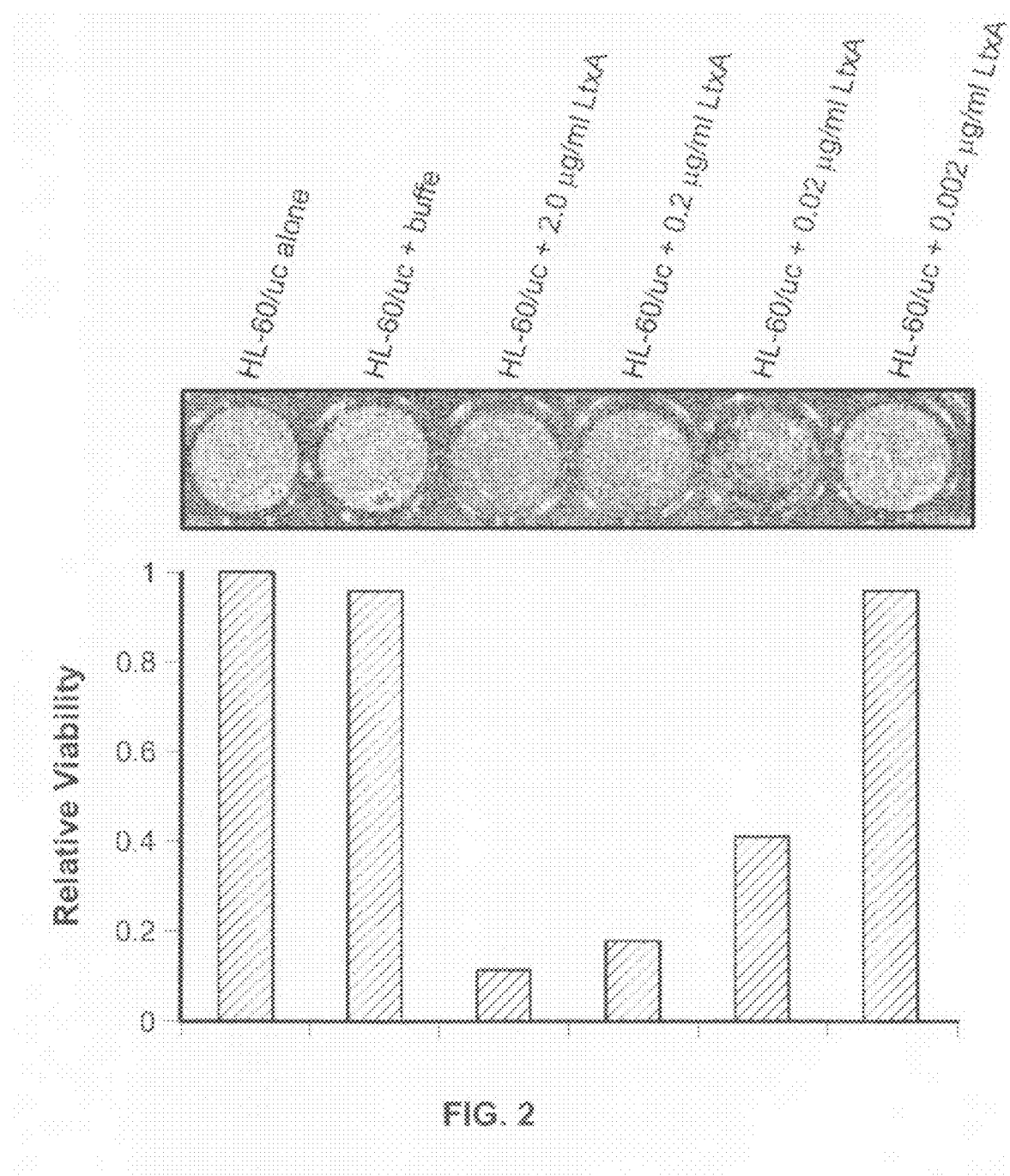
FIG. 2 is a graph showing activity data of two forms of LtxA against human red blood cells.

Data reflecting the sensitivity of HL-60luc cells to leukotoxin is shown in FIG. 2. The activity of purified leukotoxin against HL-60luc cells in vitro is quantified. The leukotoxin used in this experiment was LtxA isolated from the NJ4500 strain of *Actinobacillus actinomycetemcomitans*. The just-mentioned NJ4500 strain of *Actinobacillus actinomycetemcomitans* was deposited on Mar. 2, 2011 under the terms of the Budapest Treaty with American Type Culture Collection (ATCC), located at 10801 University Blvd. Manassas, VA 20110, where the deposited strain was given Accession Number PTA-11721. The LtxA was mixed with HL-60luc cells at various concentrations as indicated, and incubated for two hours, and then imaged with the IVIS 50 instrument. Relative viability was calculated by quantifying the number of photons produced in each well. Significant cell death was observed after two hours for concentrations of 2.0 µg/ml, 0.2 µg/ml, and 0.02 µg/ml.

To determine if the leukotoxin LtxA has activity in vivo, two Swiss Webster mice were injected i.p. with $10^6$ HL-60luc cells. One of the mice was injected with 8 µg of LtxA i.p. immediately following HL-60luc cell injection. Both mice then received an i.p. injection of luciferin substrate. The mice were monitored by in vivo bioluminescence imaging with an IVIS 50 imaging system immediately following injection of the luciferin. The luminescent signal was visible and intense in the control mousee that did not receive the LtxA injection. In contrast, the mouse that received LtxA showed essentially no luminescent signal, showing that the LtxA had killed the HL-60luc cells in vivo.

Forms of LtxA include the JP2 form (isolated from the JP2 strain of *Actinobacillus actinomycetemcomitans*) and the NJ4500 form (isolated from the NJ4500 strain of *Actinobacillus actinomycetemcomitans*). NJ4500 LtxA is well tolerated by the Swiss Webster mice. Two mice, weighing approximately 45 grams each, were injected with 10 µg of NJ4500 LtxA intravenously. These mice were monitored over a five-month period, and during this period, the mice remained healthy, did not lose weight, and had no apparent adverse reaction to the LtxA.

Figure 3:
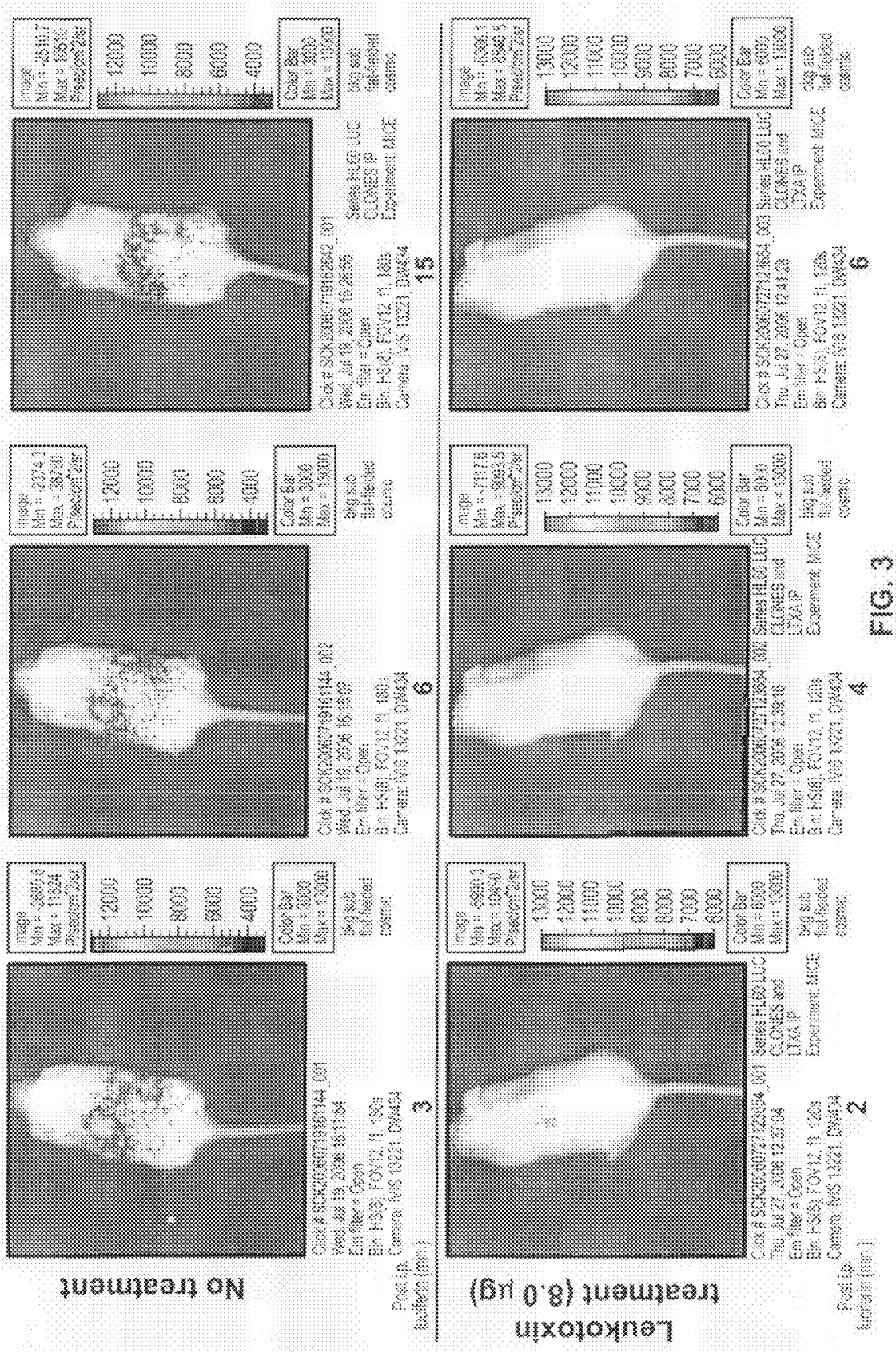
FIG. 3 is a series of images showing the effectiveness of NJ4500 LtxA in vivo.
Figure 4:
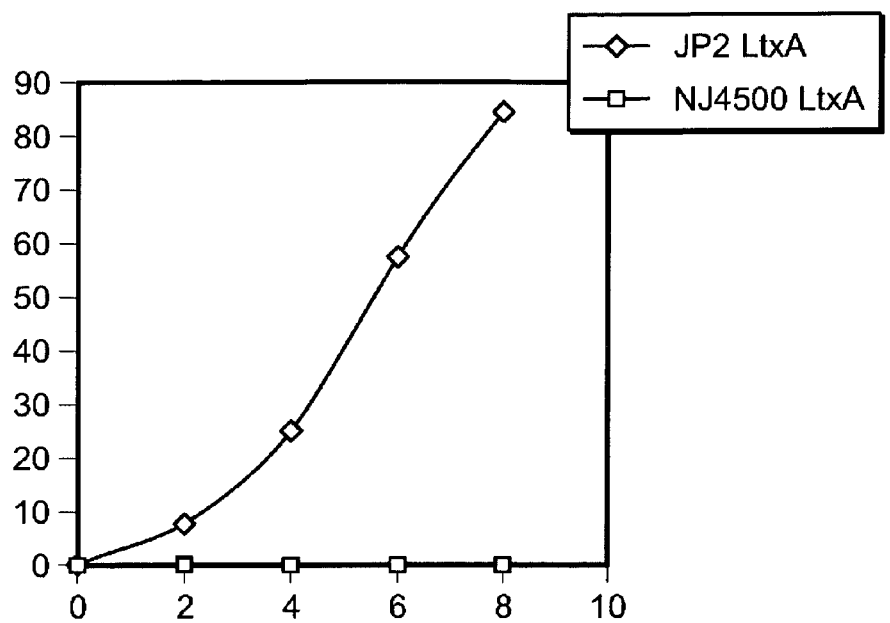
FIG. 4 a bar graph representation of data showing the sensitivity of human red blood cells to the JP2 and NJ4500 forms of LtxA.
Figure 5:
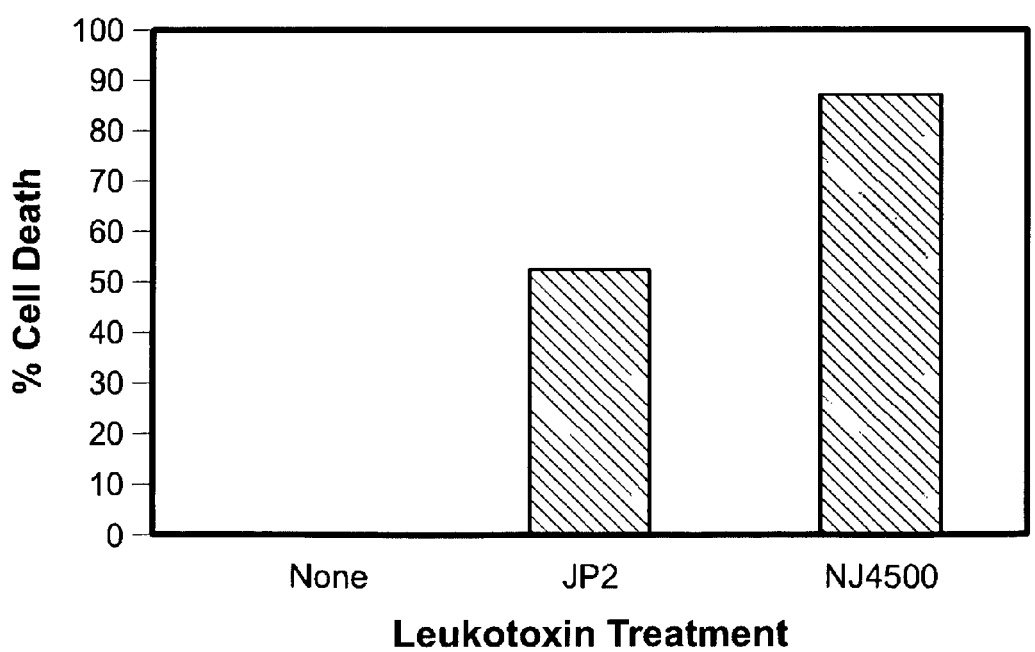
FIG. 5 is a bar graph representing data on the toxicity of the JP2 and NJ4500 forms of LtxA against HL-60 cells.

The individual forms of LtxA show different cell specificity. The NJ4500 and JP2 forms of LtxA demonstrate specificity to different types of blood cells, as demonstrated in FIG. 4. The JP2 form of LtxA is lethal to human red blood cells, whereas human red blood cells are insensitive to the NJ4500 form of LtxA. Thus, the NJ4500 form of LtxA is lethal to HL-60 cells (as shown in FIG. 3), but innocuous to human red blood cells (as shown in FIG. 4). The JP2 form is quite lethal to human red blood cells, but as shown in FIG. 5, is less deadly to leukemia cells than the NJ4500 form. The data displayed in FIG. 4 was collected by a trypan blue dye excusion assay. Leukotoxin protein LtxA (2 µg/ml) was added to $1\times10^6$ HL-60 cells, and were incubated for 90 minutes at 37° C. The cells were measured for viability with the trypan blue dye exclusion assay.

The activity of the JP2 and NJ4500 forms of LtxA against HL-60 cells differs dramatically. In FIG. 5, a bar graph representing the toxicity of the two forms of LtxA against HL-60 cells. As shown by the bar graph, the NJ4500 form of LtxA is much more lethal to the leukemia cell line than the JP2 form of the protein. Accordingly, not only is the NJ4500 form of LtxA non-lethal to human red blood cells (unlike the JP2 strain of LtxA), but the NJ4500 strain of LtxA is more lethal to leukemia cells than the JP2 strain of LtxA, thus indicating that the NJ4500 form of LtxA is a desirable leukemia or blood disease treatment as it is highly toxic to leukemia cells, but not to human red blood cells. LtxA provides a highly specific approach to treat hematologic malignancies, such as leukemia, lymphoma, and myeloma, without damaging other blood cells, such as red blood cells.

The data displayed in FIG. 5 was collected using a trypan blue exclusion assay. HL-60 cells were mixed with 2 µg/ml final concentration of LtxA from JP2 and NJ4500 as indicated and incubated for 90 minutes at 37° C. Equal amounts of LtxA from either strain were mixed with approximately $5\times10^6$ cells/ml of HL-60 cells and incubated for ninety minutes. Cell death was then assayed using the trypan blue dye exclusion assay. LtxA from NJ4500 was more effective at killing HL-60 cells than was LtxA from JP2. The toxin from NJ4500 was approximately twice as active and this result was highly reproducible for even different preparations of LtxA over four different experiments.

The NJ4500 strain of LtxA is also active in whole human blood. Whole human blood was mixed with LtxA (2.0 µg/ml final conc.) and incubated for 4 hours at 37° C. The mixtures were then mixed with red blood cell (RBC) lysis buffer (eBioscience) and the RBCs were lysed according to the manufacturer's protocol. The remaining white blood cells (WBCs) were then resuspended in PBS and cells were counted using a ViCell counter (Beckman Coulter), which employs the trypan blue dye assay to measure viability. The sample that was not treated with LtxA had 93% viability, while the sample that was treated with LtxA had a viability of 42%. Because the RBC's were lysed and removed before viability was measured, the viability measurement assesses only the viability of the remaining white blood cells. The NJ4500 LtxA caused death in nearly 60% of the white blood cells.

NJ4500 LtxA displays unique sensitivity among the blood cells found in whole blood. At a concentration of 20 µg/ml, LtxA from NJ4500 showed a high level of specificity in inducing cell death in human whole blood. After four hours incubation at 20 µg/ml LtxA, the red blood cells, basophils, and lymphocytes suffered no significant cell death. In contrast, the 60% of the white blood cells were killed, and approximately 95% of the neutrophils, monocytes, and eosinophils were killed by the LtxA.

Figure 6:
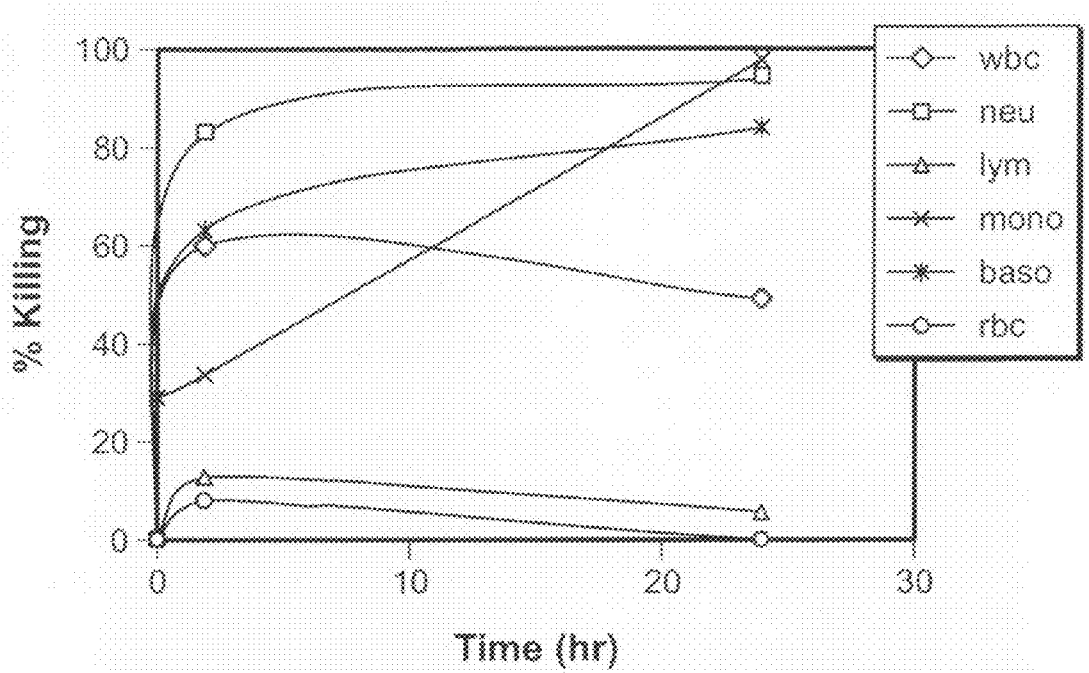
FIG. 6 is a graph of time vs. cell death for various cell types in whole human blood during incubation with 0.2 µg/ml NJ4500 LtxA.

Similar specificity was shown over time at lower doses of NJ4500 LtxA. FIG. 6 is a graph representing data that was collected over time, and shows that NJ4500 LtxA specifically target certain blood cell types. Neutrophil cells appear most sensitive to the relatively low concentration of 0.2 µg/ml LtxA with nearly 80% of neutrophils killed in only one hour. Both basophils and white blood cells (or leukocytes) were killed rapidly by the NJ4500 with about 60% of the cells dying within an hour. Monocytes are quite sensitive to NJ4500 LtxA, as nearly 100% of the monocytes died, however significant amounts of cell death required longer incubation periods. In contrast, red blood cells (erthrocytes) and lymphcytes were completely insensitive to 0.2 µg/ml NJ4500 LtxA over time.

All histological data presented herein was collected through histology examinations. The blood samples were smeared onto a glass slide and then processed and stained on a Coulter LH slide maker, using a Wright stain for differentials.

The JP2 and NJ4500 forms of LtxA isolated *Actinobacillus actinomycetemcomitans* differ functionally in that the NJ4500 shows greater toxicity towards leukemia cells, along with greater specificity. The NJ4500 form of LtxA is highly specific towards white blood cells (leukocytes). Specifically, the NJ4500 form of LtxA is highly specific towards basophils, neutrophils, and monocytes. The NJ4500 form of LtxA is also highly specific towards eosinophils. This form does not induce significant cell death in red blood cells (erythrocytes) or lymphocytes. These functional distinctions may be related to structural modifications. Specifically, NJ4500 LtxA is highly modified with fatty acids.

Figure 7:
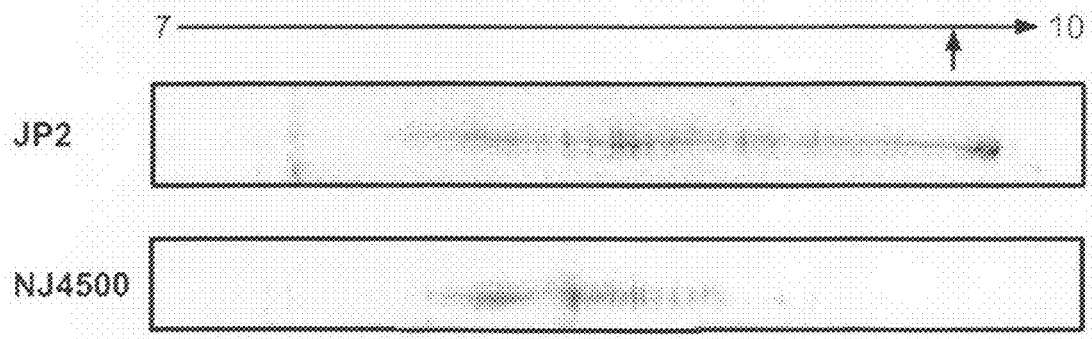
FIG. 7 is a two-dimensional gel electrophoresis of two forms of LtxA.

A two-dimensional gel electrophoresis of JP2 and NJ4500 LtxA is shown in FIG. 7. The gel shown in FIG. 7 shows that the JP2 form of LtxA contains a significant amount of protein with an isoelectric point of at least 9.0. To create the 2-D gel, LtxA (20 mg) from JP2 or NJ4500 was separated first by isoelectric point through a pH gradient of 7-10. LtxA separated by isoelectric focusing was then separated by mass using polyacrylamide gel electrophoresis. Protein was visualized with SYPRO ruby stain. The LtxA samples were prepared for 2-D gel electrophoresis by processing 20 mg with a 2-D gel clean-up kit according to the manufacturer's directions (Amersham Biosciences, Piscataway, N.J.). Following the clean-up, the pelleted protein was resuspended in 182 ml rehydration buffer (Bio-Rad, Hercules, Calif.) and mixed with 3.7 ml DTT (500 mg/ml) and 2 ml 1% bromophenol blue. The sample was then loaded onto a pH 7-10 IPG strip and processed for isoelectric focusing according to the manufacturer's protocol (Bio-Rad, Hercules, Calif.). After isoelectric focusing, the IPG strip was layered atop a 10% polyacrylamide gel and resolved in SDS buffer for several hours. Visualization of protein spots was accomplished by staining the gel in SYPRO ruby protein stain (Bio-Rad, Hercules, Calif.).

Two other RTX toxins, *E. Coli* HlyA and *B. pertussis* CyaA, are modified covalently with fatty acid moieties at internal lysine residues. In *E. Coli*, hlyC is a fatty acyl transferase and is required for modification of HlyA. Based on the presence of an hlyC homologue in *A. actinomycetemcomitans* (ltxC), it is predicted that *A. actinomycetemcomitans* LtxA is also modified. Modification of HlyA and CyaA is required for toxin activity and the degree of modification is directly correlated with toxicity.

The two forms of LtxA were subjected to two-dimensional gel electrophoresis to assess whether differential modification of the proteins accounted for the functional differernces. The two-dimensional gel electrophoresis showed that LtxA from both strains exists in multiple isoforms (See FIG. 7). Several representative spots were excised and subjected to trypsin digestion and MALDI-TOF MS analysis. MALDI-TOF MS confirmed that all species were *A. actinomycetemcomitans* LtxA (data not shown).

The predicted pI of LtxA based on primary amino acid sequence is approximately 9. (Represented by the rightmost spot and small arrow in FIG. 7). Modification of lysine residues with fatty acids shifts the pI towards the acidic end, therefore, a greater fraction of the NJ4500 LtxA is modified compared to LtxA from JP2.

Approximately half of the JP2 LtxA is completely unmodified (as represented by the dense spot at approximately pI 9.). In contrast, none of the NJ4500 LtxA appears to be completely unmodified in the 2-D gel shown in FIG. 7.

Other RTX toxins are modified with fatty acids and this modification is required for activity. Modification of RTX toxins may contribute to host and cell type specificity. *E. coli*, a-hemolysin, is modified at two internal lysine residues with C14, C15, or C17 fatty acid residues. Because *E. coli* can incorporate into HlyA three different fatty acids at two different lysine residues, preparations of HlyA are heterogeneous. Based on the two-dimensional gel electrophoresis data shown in FIG. 7, LtxA is even more heterogeneous than HlyA.

LtxA has approximately 100 lysine residues and modification at several of them with different types of fatty acids accounts for the relatively large number of different isoforms. LtxA purified from NJ4500 is more active than LtxA from the JP2 strain. Nearly all of NJ4500 LtxA existed in some type of modified form whereas preparations of JP2 LtxA contained a significant amount of unmodified form (FIG. 7). Consistent with other RTX toxins, the unmodified toxin from JP2 is inactive against HL-60 cells. Thus, the percent of active LtxA molecules in preparations from NJ4500 is greater than from JP2.

A fatty acid is defined as a long-chain monobasic organic acid or a hydrocarbon chain. Fatty acids associated with NJ4500 LtxA were analyzed by Mylnefield Research Services, Lt., the Lipid Analysis Unit, Scotland. The protocol for analysis of myristoylated proteins described by Neubert, T. A. and Johnson, R. S. (Methods Enzymol., 250, 487-494 (1995)) was followed. It involves acidic hydrolysis of the protein, followed by acid catalysed methylation of the fatty acids for analysis by gas-chromatography. Approximately 3 mg of LtxA was subjected to this protocol, and preliminary data shows that at least myristic acid (C14) and palmitic acid (C16) are present in the LtxA protein.

The pI values of the two-dimensional gel indicated that basic residues are modified (making the protein more acidic). Any basic residue may be chemically modified by a fatty acid to reduce the pI. Because it is known that the lysine residues of RTX family members are modified by fatty acids, and that such a chemical modification increases activity of the RTX familiy members, the LtxA protein is likely to be modified at lysine residues.

Based on the data collected to date, the specificity and increased activity evident in the NJ4500 form of LtxA can be attributed to the composition of leukotoxin proteins with greater than 85% of the leukotoxin proteins chemically modified at a basic amino acid residue. This composition is an LtxA composition isolated from a bacterium such as *Actinobacillus actinomycetemcomitans*, and preferably the NJ4500 strain of *Actinobacillus actinomycetemcomitans*.

This composition as described induces cell death in myeloid leukocytes. The composition is specific to any of white blood cells, neutrophils, monocytes, basophils, and eosinophils. Myeloid cells are cells belonging to the white blood cell lineage, and consist of granulocytes (basophils, neutrophils, eosinophils), monocytes, erythrocytes and platelets. The LtxA composition is specific as it is substantially non-toxic to lymphoid leukocytes.

White blood cells are a type of cell formed in the myelopoietic, lymphoid, and reticular portions of the reticuloendothelial system. Lymphocytes are a white blood cell formed in the lymphatic tissue throughout the body (eg. Lymph nodes, spleen, thymus, tonsils, Peyer patches, and sometimes in the bone marrow). In normal adults approximately 22-28% of the total number of white blood cells in the circulating blood are lymphocytes.

The specificity of the NJ4500 LtxA is especially useful as a treatment against acute myeloid leukemia (AML) and chronic myeloid leukemia (CML) because these are diseases in which only the myeloid cells are malignant. Thus, LtxA provides a high level of toxicity to certain myeloid cells, while leaving the red blood cell population unharmed, as the NJ4500 is substantially non-toxic to lymphocytes and red blood cells.

As discussed above, the NJ4500 LtxA composition of the invention includes chemical modifications, and the chemical modifications include fatty acid modifications to basic amino acid residues. Preferably, the basic amino acid residue that is modified is a lysine residue, and greater than 90% of the leukotoxin proteins are chemically modified at at least one basic amino acid residue.

Also discussed above, the NJ4500 LtxA compositions of the invention have a pI less than 9. Within the composition, 85% of the leukotoxin proteins have a pI less than 9.0. In another embodiment, 90% of the leukotoxin proteins have a pI less than 9.0, and in yet another embodiment, 95% of the leukotoxin proteins have a pI less than 9.0. In still another embodiment, 100% of the leukotoxin proteins have a pI less than 9.0.

As shown in FIG. 7, most of the NJ4500 LtxA proteins have a pI less than 8.5. In one embodiment of the invention, 85% of the leukotoxin proteins have a pI less than 8.5, and in another embodiment, 90% of the leukotoxin proteins have a pI less than 8.5. The invention includes compositions where 95% of the leukotoxin proteins have a pI less than 8.5, and in yet another embodiment, 100% of the leukotoxin proteins have a pI less than 8.5. The leukotoxin proteins are isolated from *Actinobacillus actinomycetemcomitans*, and in another embodiments, the leukotoxin proteins are isolated from the NJ4500 strain of *Actinobacillus actinomycetemcomitans*.

Because NJ4500 demonstrates a unique specificity among RTX family members, one embodiment of the present invention includes an RTX family protein that selectively lyses white blood cells more effectively than red blood cells. The RTX family member is substantially non-toxic to red blood cells.

Also provided is a pharmaceutical composition comprising leukotoxin proteins and a pharmaceutically acceptable carrier, along with a method of selectively inducing cell death in myeloid leukocytes comprising contacting the myeloid leukocytes with a composition comprising leukotoxin proteins.

In another embodiment, a method of killing a target cell by contacting the target cell with leukotoxin proteins is provided. In this method each leukotoxin protein has a pI less than 9.0. In one embodiment of this method, the myeloid leukocyte cells die at a faster rate than lymphoid cells.

In still another embodiment, a method of treating a blood disease is provided. This method comprises administering a composition of leukotoxin proteins isolated from the NJ4500 strain of *Actinobacillus actinomycetemcomitans* to a subject suffering from the blood disease. In treating a blood disease, a chemotherapeutic pharmaceutical may be administered to the subject in conjuction with the leukotoxin. Some appropriate chemotherapeutic pharmaceuticals include idarubicin, cytarabine, etosposide, daunorubicin, mitoxantrone, and melphalan. Other common chemotherapeutic agents for the treatment of leukemia and lymphoma include Chlorambucil, Fludarabine phosphate, Cytarabine, and Daunorubicin hydrochloride. These drugs share the common property of being highly toxic to humans, affecting many different tissue and organ systems of the body. Bone marrow suppression, severe neurologic effects, infertility, pulmonary, and gastrointestinal effects are some of the adverse effects exhibited by these drugs. Many of the drugs act by inhibiting DNA synthesis, a process that all dividing cells carry out. Most cells of the body are targeted by these non-specific pharmaceuticals. Any suitable pharmaceutical agent may be used in conjunction with LtxA, and the combination of a pharmaceutical agent with leukotoxin is intended to reduce the dose of the pharmaceutical necessary to achieve effective results in patients.

In addition to the potential uses as an anti-cancer agent, *Actinobacillus actinomycetemcomitans* leukotoxin may serve as a potent anti-viral. Specifically, HIV replicates and resides inside macrophages and T-lymphocytes. Viruses are difficult to combat because they often "hide" from the immune system inside host cells. Leukotoxin could destroy those macrophages that are infected with HIV, allowing the virus to be released and attacked by the natural host immune defenses. This treatment would be different in that the therapy would not be directed against the virus (which would select for resistant HIV mutants), but rather against the host cell in which the virus resides.

In one embodiment the blood disease is leukemia, lymphoma, or myeloma, and in another embodiment, leukotoxin is used in a method of selectively sensitizing myeloid leukocyte cells to permeates. This method comprises contacting the myeloid leukocyte cells with a composition comprising leukotoxin proteins, wherein each leukotoxin protein has a pI less than 9.0, and lymphoid cells are substantially unsensitized to permeates by the composition.

In another embodiment, a method of purifying a RTX family protein from *Actinobacillus actinomycetemcomitans* comprises:

a. inoculating a single colony of *Actinobacillus actinomycetemcomitans* into a fresh broth and growing cultures;
b. adding the growing cultures to fresh broth, adding beads and incubating;
c. centrifuging the incubated culture, forming a pellet and a supernatant;
d. filtering the supernatant through a membrane to provided a filtered supernatant:
e. mixing $(NH_4)_2SO_4$ and the filtered supernatant together to form a mixture;
f. centrifuging the mixture to form a mixture pellet;
g. resuspending the mixture pellet in buffer to form a protein resuspension;
h. passing the protein resuspension through a column; and
i. collecting the protein eluting off the column.

In a further aspect of the invention, an assay system and method are presented, that enables the testing of anti-cancer drugs such as the leukotoxins of the present invention, under physiological conditions, with the consequence and benefit that a relevant prediction of activity is rapidly and efficiently obtained.

Screens for compounds and proteins with anti-cancer activity employ viability assays using relevant cancer cell lines. For leukemia studies, the human leukemia cell line, HL-60, is often used as a model system. To facilitate the discovery and investigation of anti-leukemia therapeutics under physiological conditions, and in accordance with this invention, a bioluminescent HL-60 cell line has been engineered that can be visualized in whole human blood and living mice and whose viability can be rapidly determined. A WBC-specific bacterial toxin has been shown to be active in blood. The engineered HL-60luc cells of the invention behave similar to the parental HL60 cell line. When used in a bioluminescence imaging assay (BLI) as discussed in detail herein, the BLI signal peaked approximately one hour following the addition of luciferin but remained relatively high for several hours. This type of in vitro kinetics where an early peak in luminescence is followed by a slow decline is consistent with other BLI cell lines. The detection limit of 1000 viable cells is also consistent with other reports (35,36). Because human blood contains plasma proteins, such as antibody and proteases, and other cells, that may affect the activity, availability, or stability of a drug, the anti-leukemia assays with HL-60luc cells in the presence of blood can yield more physiological results than with buffer or growth media alone.

In vivo bioluminescence imaging (BLI) is a technology that allows visualization of live bioluminescent cells (mammalian, bacterial, viruses) in complex biological material and living animals (24,31). Firefly luciferase has been used extensively in reporter systems and its expression can be measured quantitatively using a luminometer or highly sensitive charge coupled device (CCD) camera. Rocchetta et al. (32) found that the CCD camera was approximately 25 times more sensitive than a luminometer, and so the IVIS 50 imaging system (Xenogen, Alameda, Calif.) was used for the work presented here. Luciferase reacts with its substrate, luciferin, to produce oxyluciferin and light (11). Because ATP and oxygen are required for the reaction, photon production has been used as a quantitative measurement of cellular viability (14). Animal studies have demonstrated a strong correlation between the abundance of emitted photons and number of cells present in a given tissue or animal (5,11).

In general, the field of oncology has utilized BLI extensively to study the effects of anti-cancer therapy in vivo (15, 23). However, application of BLI to study hematologic malignancies has been limited (6,22,44), and to date, there are no bioluminescent hematologic cell lines commercially available (Xenogen Corp., Alameda, Calif.). Validation of BLI in preclinical models has been carried out using currently available methods and evidence indicates that BLI has excellent sensitivity and offers unique advantages (5,25,31,33). For example, non-invasive BLI allows visualization of cells temporally and spatially, thus permitting small changes in cell number and localization to be detected over time (24,31). In addition, animals need not be sacrificed at each sampling time point, decreasing the number of animals that are required for an experiment and minimizing inconsistency from animal-to-animal variations.

There is a significant difference between the sensitivity of BLI and the trypan blue dye exclusion assay. For a cell to be detected as nonviable with the trypan blue assay, the dye must enter the cytoplasm of the cell. Trypan blue is a relatively large molecule (mw 960.8) and while many cells may be metabolically dead, their membranes could be sufficiently intact to exclude the dye to appear viable. In contrast, BLI detects killing sooner because ATP is no longer available in a metabolically dead cell. The results are in strong agreement with Kuzmits et al. (17) who found that an ATP/bioluminescent assay with HL-60 cells indicated nearly complete killing after a 24 hour incubation with 5.7 µmol/l doxorubicin, while the trypan blue assay indicated almost no killing after 48 hours with the same drug concentration. Furthermore, Petty et al. (30) reported that a bioluminescent ATP assay could detect as few as 1500 viable cells/well while the MTT assay could not detect less than 25,000 cells/well.

Bacterial toxins have been investigated for their anti-cancer therapeutic potential for many years. Several widely-studied toxins include diphtheriae toxin (DT) and Pseudomonas exotoxin A (PE) (16). To increase the specificity of these toxins, their toxic domains are often fused to other molecules that target the toxin to certain cell types. For example, ONTAK, a recently approved drug used to treat cutaneous T-cell lymphoma, is a fusion molecule of DT and IL-2 (10, 26).

As discussed above, the oral bacterium *A. actinomycetemcomitans* produces a 113 kDa protein toxin, leukotoxin (LtxA), which kills only blood cells of humans and Old World Primates (3739). Furthermore, and in accordance with a first aspect of the invention, a strain has been identified whose purified LtxA does not lyse RBCs. LtxA binds to LFA-1 on host cells (19) and destroys cells by apoptosis or necrosis (18). Because LtxA already has specificity towards WBCs, it has been proposed that the protein might serve as an effective targeted therapy for hematologic malignancies. In addition, the toxin kills host cells by disruption of the cell membrane (18) and therefore represents a mechanism of action that is different from other chemotherapeutic agents.

In an effort to further evaluate the therapeutic potential of LtxA, a test was conducted with the present in vivo screening assay. Accordingly, the toxic effects LtxA against HL-60luc cells in blood were examined. As set forth and demonstrated herein, the toxin remains highly active in human blood and kills HL60luc cells as efficiently as in RPMI medium. In addition, bone marrow progenitor cell proliferation assays indicate that LtxA is active toward myeloid progenitor cells and has an $IC_{50}$ value in the low ng/ml range. Preliminary studies also suggest that LtxA is active mice and does not display toxicity when injected at high doses into mice.

With the ability to rapidly determine HL-60luc cell viability in the presence of biological fluids, it is possible to efficiently screen thousands of different compounds at a time for anti-leukemia activity. Assays may be performed in 96- or 384-well dishes in the presence of physiologically-relevant samples such as blood, plasma, or hepatocytes. Indeed, an important preclinical screen to study drug biotransformation is performed in the presence of hepatic material, such as human liver microsomes, human liver cytosol fractions, and hepatocytes (3). HL-60luc cells could be used in high-throughput hepatic screens for drugs with anti-leukemia bioactivity.

In addition to using the present assay comprising the HL-60luc cells for drug discovery, the test system can be used to monitor the condition of a patient undergoing drug therapy. Accordingly, the condition and behavior of a known drug or combination of drugs in the presence of blood samples from different leukemia patients may be measured and determined. For example, neutralizing antibody in a patient's blood against a potential drug might allow a clinician to exclude the drug from the therapeutic regimen. Excluding an otherwise ineffective drug might greatly reduce unwanted side effects. Indeed several studies have shown a correlation between in vitro chemosensitivity of tumor cells and therapy outcome (34,42). Such correlations could allow the development of assay-directed individualized chemotherapy regimens. Thus the assay of the invention can be used in the following ways:
1. Screening novel drugs for anti-leukemia/cancer activity.
2. Determine the best drug dosage for a leukemia/cancer patient.
3. Determine which drug might be most effective for a leukemia/cancer patient.

EXAMPLES

The following examples are presented in order to more fully illustrate the preferred embodiments of the invention. They should in no way be construed, however, as limiting the broad scope of the invention.

EXAMPLE 1

Purification of LtxA from the NJ4500 Strain of *A. actinomycetemcomitans*

The JP2 strain of *A. actinomycetemcomitans* produces abundant LtxA, but it does not represent a fresh clinical isolate. Here, LtxA was purified from the clinical isolate NJ4500 of *A. actinomycetemcomitans*. This strain also produces and secretes a large amount of LtxA, but the cells adhere to surfaces instead of growing planktonically. This type of adherent growth results in a relatively low number of cells per volume. The cell density of adherent cells was increased by increasing the surface area on which the cells can grow through the addition of spherical glass beads. Soda lime beads provided the greatest amount of LtxA when compared to Pyrex glass beads. The amount of LtxA that was purified from NJ4500 in the presence of soda lime beads was approximately twice that of JP2.

It is important to note that growth of *A. actinomycetemcomitans* in the presence of both types of glass beads was similar suggesting that differences in LtxA quantity was not due variable growth. *A. actinomycetemcomitans* strains JP2 and NJ4500 are known in the art. All bacteria were grown in *A. actinomycetemcomitans* growth medium (AAGM) as known in the art. Plates were incubated at 37° C. in 10% $CO_2$ for 4 days. Broth cultures were incubated for 24 h unless otherwise noted.

LtxA was isolated from JP2 by growing cells in 5 ml AAGM broth for 7-9 h and then diluted into 400 ml fresh AAGM broth. These cultures were then grown for 13-17 h before harvesting supernatant. To obtain supernatant, cultures were centrifuged at 17,000 g for 10 minutes at 4 8 C. The supernatant was filtered through a 0.22 mm low-protein binding membrane filter. For every 100 ml of filtered supernatant, 32.5 g $(NH_4)_2SO_4$ was added. The mixture was gently rocked at 4 8 C for 1 h. The precipitated protein was collected by centrifugation at 10,000 g for 20 min at 4 8 C. The pellet from 400 ml supernatant was then resuspended in 2 ml LtxA buffer (20 mM Tris-HCl, pH 6.8, 250 mM NaCl, and 0.2 mM $CaCl_2$).

The resuspended pellet was loaded on a column packed with 40 ml of Sephadex G-100 (Sigma, St. Louis, Mo.). Protein was eluted in 1 ml fractions with LtxA buffer. Protein content in each fraction was determined with the Bradford reagent. The three fractions with the highest protein content were combined, aliquoted and stored at −80° C. The purity of LtxA was determined on a 4-20% SDS-PAGE gel and the concentration was determined by the BCA assay according to the manufacturer's protocol (Pierce, Rockford, Ill.).

LtxA was purified from the adherent strain NJ4500 by first growing cells in tubes filled with 5 ml AAGM broth for 14 h and then transferring 20 ml of growing cultures into 400 ml AAGM broth in a 500-ml bottle. Prior to adding 400 ml sterile AAGM broth to the 500 ml-bottle, 300 g of glass beads (or no beads, for controls) were autoclaved inside the bottle. The soda lime beads were obtained from Fisher Scientific (cat. 11-312C) and pyrex beads from Corning Incorporated (cat. 7268-5). The inoculated bottle was grown for 36-40 h as described above. During growth, the bottle was inverted several times to allow adherent cells to coat all the beads. After growth, the broth was removed and centrifuged and processed as described above for JP2 LtxA. For these experiments, cells were not removed from the beads.

Although adherent variants such as NJ4500 retain a greater amount of LtxA than the nonadherent variants, a large amount of secreted LtxA from NJ4500 can still be harvested. Because NJ4500 attaches avidly to surfaces, the number of growing cells per volume can be increased by adding 5 mm glass beads to the growth medium. In methods using one of two different types of glass beads, Pyrex and soda lime, the yield of LtxA from cells growing on Pyrex was significantly reduced when compared to the control of no glass beads or soda lime beads.

EXAMPLE 2

Imaging of Mice Injected with HL-60luc

The images of the mice shown in FIG. 3 were collected using in vivo bioluminescence imaging. The SCID mouse model has been used extensively for the study of hematologic malignancies, and the pattern of leukemia displayed in SCID mice closely resembles human clinical disease. In the model, leukemia cells are injected into SCID mice, usually intravenously. A commonly used leukemia cell line is HL-60, originally isolated from a 36-year-old female patient with acute promyelocytic leukemia. Animal studies have shown that HL-60 cells can infiltrate bone marrow, the spleen, thymus, kidney, liver, lungs, and even the brain. It has been reported that the mean survival time for SCID mice that were injected with HL-60 cells was 42.5 days following injection; however, this time can vary depending on the passage state of the HL-60 cells being injected.

In vivo bioluminescence imaging (BLI) is a technology that allows visualization of live bioluminescent cells (mammalian, bacterial, viruses) in a living animal, without sacrificing the animal. Cells to be visualized are engineered to express luciferase, which reacts with its substrate, to result in light production. Because the reaction also requires ATP, bioluminescence has also been used as a measure of viability. In bacteria, the substrate is encoded within the same operon as the luciferase enzyme. In the mammalian system, the substrate, luciferin, must be injected separately into the animal for the light-producing reaction to take place. Visualization of luminescent cells requires a highly-sensitive CCD camera that can detect low-level light within a short period of time. We currently maintain the Xenogen IVIS 50 imaging system for this purpose (Xenogen Corp., Alameda, Calif.). The distribution and abundance of luciferase-producing cells can be quantified by anesthetizing the animals and imaging them with the IVIS 50 imaging system.

BLI allows visualization of cells temporally and spatially, thus allowing small changes in cell number and localization to be detected over time. In contrast, using standard methods, animals must be sacrificed and extensive histological examination performed to localize cells in question. In general, the field of oncology has utilized BLI extensively, however, application of BLI to study hematologic malignancies has been limited, and to date, there are no bioluminescent hematologic cell lines commercially available (Xenogen Corp., Alameda, Calif.).

In the oncology models, engineered malignant cells are injected into animals and the progression of cancer is observed. In addition, transgenic light-producing mice are available for use in several oncology models (Xenogen Corp., Alameda, Calif.). Metastasis and regression can be monitored with great sensitivity and efficiency with the IVIS instrument. Of great significance, the effects of anticancer therapy can be determined before the endpoint of death is reached.

EXAMPLE 3

Prepareation of Assay System

Experimental
Cells and Growth Conditions.

HL-60 cells were obtained from American Type Culture Collection (ATCC) and maintained in RPMI +10% fetal bovine serum (FBS) (Invitrogen, Carlsbad, Calif.) at 37° C.+5% $CO_2$. *Escherichia coli* was grown in LB medium at 37° C. *A. actinomycetemcomitans* strains were grown in AAGM at 37° C.+10% $CO_2$ as previously described (12).
DNA Manipulations.

The luciferase-encoding plasmid for transfecting HL-60 cells was constructed by cloning luciferase gene from pGL3 (Promega, Madison, Wis.) into the geneticin resistance gene-containing plasmid pCI-neo (Promega, Madison, Wis.). Both plasmids were digested with BglII and XbaI and the Neo-containing fragment was then ligated to the pGL3 fragment that contained the luciferase gene. The mixture was transformed into *E. Coli* and the bacteria were selected on LB+carbenecillin (50 μg/ml). Plasmid from bacteria was prepared using the plasmid miniprep kit (Qiagen, Valencia, Calif.). The new plasmid, encoding both luciferase and geneticin, was designated pMP1.

The plasmid, pMP1, was transfected into HL-60 cells by electroporation. Briefly, 106 cells were resuspended in 400 μl electroporation buffer (20 mM HEPES pH 7.0, 137 mM NaCl, 5 mM KCl, 0.7 mM $Na_2HPO_4$, 6 mM glucose, 0.1 mM β-mercaptoethanol). Plasmid pMP1 was added at a concentration of 12.5 μg/ml and the mixture was incubated for 5 minutes on ice. The mixture was added to a cuvette and a pulse of 380 V was administered. Five ml of fresh RPMI medium was added to the cells and they were grown for 24 hours before geneticin was added.

Preparation of Cytotoxic Agents.

Bacterial leukotoxin (LtxA) was purified from *A. actinomycetemcomitans* as previously described (7). LtxA was stored in 100 μl aliquots at −80° C. until used. A stock solution of chlorambucil (Sigma, St. Louis, Mo.) was prepared by dissolving 30 mg into 1 ml of DMSO. The drug was freshly prepared prior to each experiment.
Bioluminescent Imaging (BLI).

For detection of bioluminescence (BL) from cultured HL-60luc cells, 200 μl of cells were mixed with 1 μl luciferin (15 mg/ml) and then imaged with the IVIS 50 imaging system (Xenogen Corp., Alameda, Calif.). For animal studies, Swiss Webster mice were first injected with 106 HL-60luc cells (resuspended in PBS) or PBS control intraperitoneally (i.p.) or intravenously (i.v.). Mice were then anesthesized with acepromazine (0.3 mg/40 g, i.p.) and a rodent cocktail [ketamine (20 mg/ml) and xylazine (2.5 mg/ml)] (0.1 ml/25 g, i.p.). Luciferin was then injected (150 mg/kg) i.p and the mice were imaged with the IVIS 50 instrument at different times. Images were analyzed using the Living Image Software (Xenogen Corp., Alameda, Calif.).

RESULTS

Construction of a Stable HL-60 Luciferase-expressing Cell Line.

Figures 8A, 8B:
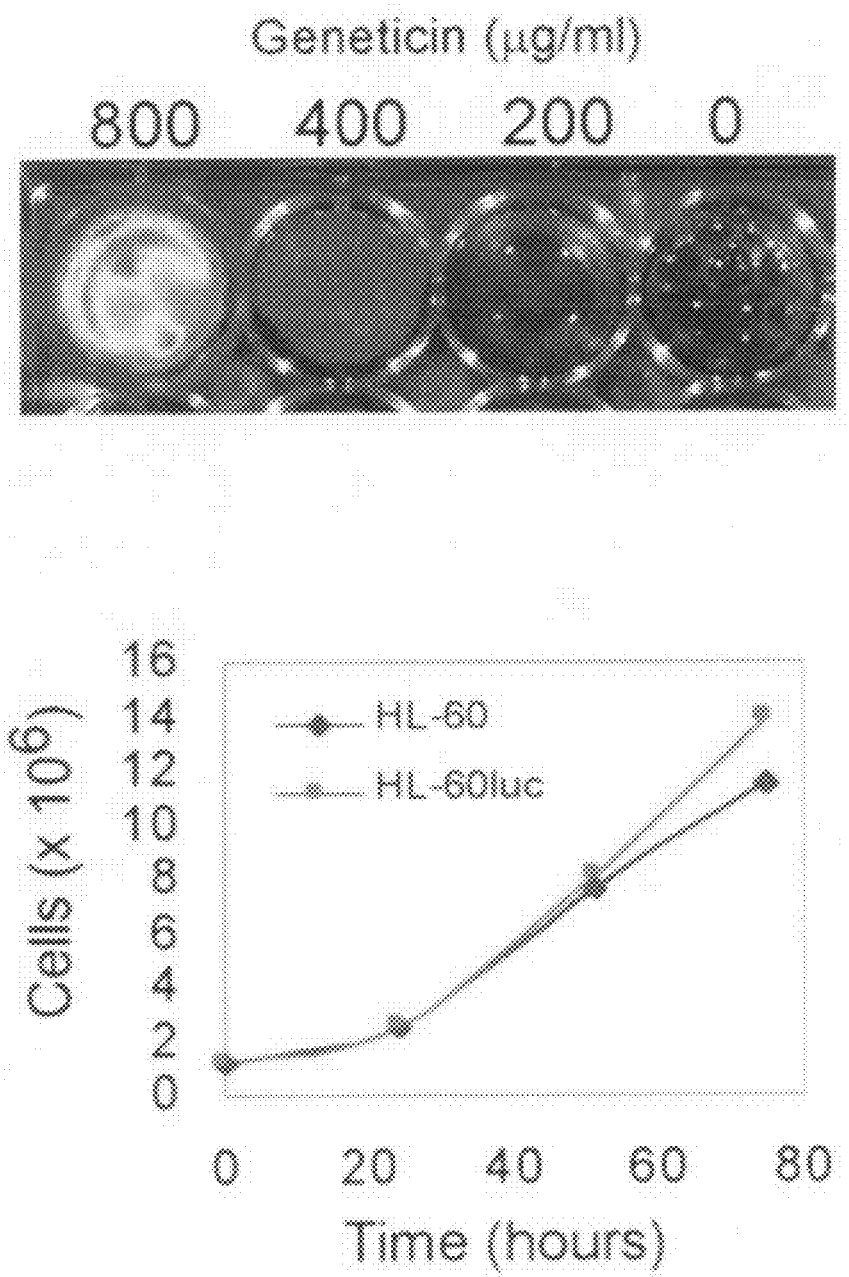
FIGS. 8A and 8B show the construction of a stable luciferase-expressing HL-60 cell line wherein (A) HL-60 cells were transfected with pMP1 and then grown in wells with different concentrations of geneticin. Bioluminescence was detected with the IVIS 50 instrument and (B) Growth curves for parental HL-60 and engineered HL-60luc cells. Cells were grown in RPMI as described and viable cells were counted with the ViCELL cell counter.

To generate an HL-60 cell line that stably expresses luciferase, a plasmid was constructed by cloning the luciferase gene from pGL3 into the geneticin resistance gene-containing plasmid pCI-neo. The modified plasmid, pMP1, was then electroporated into HL-60 cells (obtained from ATCC) and grown under geneticin selection. When geneticin was included in the growth medium to select for the plasmid, bioluminescence (BL) was observed, indicating that cells received the luciferase-encoding plasmid. FIG. 8A shows HL-60 cells that were transfected with pMP1 and then grown in wells with different concentrations of geneticin. Bioluminescence was detected with the IVIS 50 instrument. Cells were grown for 8 weeks longer to allow the generation of stable clones. After 8 weeks, geneticin selection was removed to determine if the luciferase-encoding gene had successfully integrated into the genome. Even after growing cells for many generations without selection, the HL-60 cells still emitted light, suggesting that stable transfectants had been obtained.

To continue studies, a homogeneous population of cells derived from a single stable clone was isolated by performing minimal dilutions with stable transfectants. Cells were diluted to approximately one cell/well in a 96-well dish and then examined microscopically to exclude wells that received more than one cell. Dishes were further incubated and then imaged with the IVIS 50 instrument. Cells were transferred to larger dishes, grown and then and saved in liquid nitrogen. Viability of these saved cells was greater than 90%.

An important property for BLI studies is photon flux per cell (photons/second/cell). The flux/cell for one specific clone that was used in all subsequent assays described here was calculated. The calculated value of 16 photons/second/cell is consistent with values obtained from other engineered cell lines (Xenogen Corp., Alameda, Calif.). It is believed that this is the first HL-60 cell line that has been engineered to stably express luciferase.

To confirm that the engineered HL-60 cells maintain basic growth characteristics, growth studies were performed comparing HL-60luc cells to parental HL-60 cells. Cells were grown in RPMI with 10% FBS and then counted with a Vi-CELL cell viability analyzer (Beckman Coulter, Inc., Miami, Fla.). Growth curve experiments in RPMI for the two cell lines indicated that HL-60luc cells behave like the parental cell line. FIG. 8B shows growth curves for parental HL-60 and engineered HL-60luc cells. Cells were grown in RPMI as described and viable cells were counted with the ViCELL cell counter.

Detection of HL-60luc in Blood.

Figure 9A:
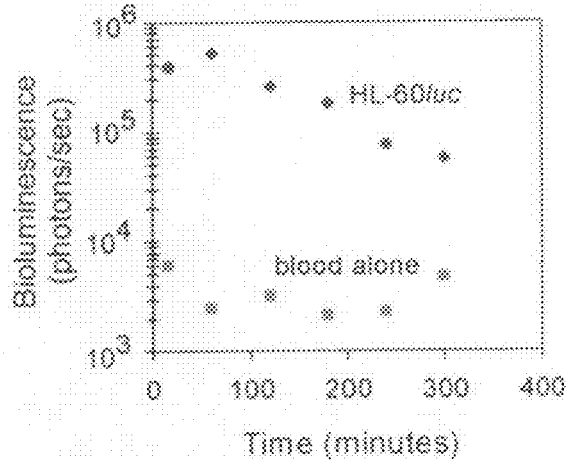
FIGS. 9A-9C shows the detection of HL-60luc cells in whole blood including (A) Kinetics of BL over time. HL-60luc cells were mixed with blood and luciferin and then imaged with the IVIS 50 instrument at the indicated time points. The observed pattern was highly reproducible. (B) Detection limit of HL-60luc cells. Cells were mixed with blood and luciferin and then incubated for one hour before imaging. (C) The number of HL-60luc cells shows a linear correlation with BL.

To determine the kinetics of bioluminescence in blood, $6\times10^5$ HL-60luc cells were mixed with human peripheral blood and luciferin was added to the mixture. BL was then measured over time as photons/second from each sample. FIG. 9A shows the kinetics of BL over time. HL-60luc cells were mixed with blood and luciferin and then imaged with the IVIS 50 instrument at the indicated time points. The observed pattern was highly reproducible. The signal peaked at one hour and was approximately 200 times greater than the background signal from blood alone. FIG. 9A. These results were highly reproducible and a similar pattern was obtained when the same experiment was performed in RPMI. BL values in RPMI were approximately two-fold greater than in blood likely due to light absorption by the blood.

Figure 9B:
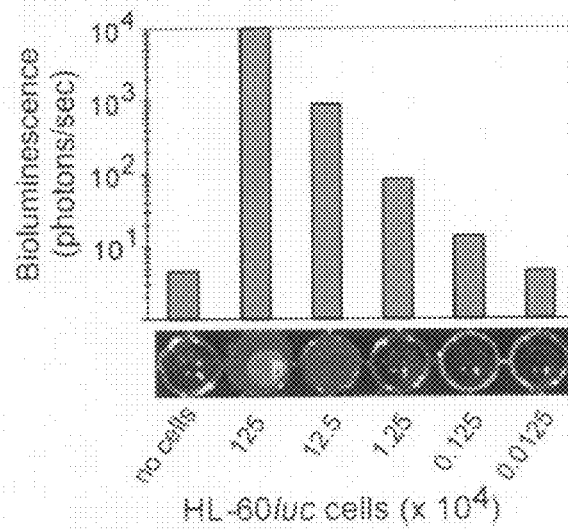
Figure 9C:
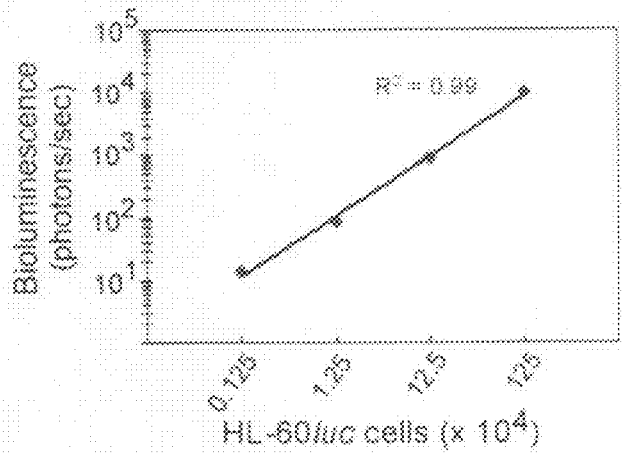

The sensitivity of detection in blood was then determined. Different numbers of HL-60luc cells were mixed with blood (200 μl total) and luciferin was added to each sample. The mixtures were incubated at 37° C. for one hour and BL was measured. FIG. 9B shows detection limit of HL-60luc cells. Cells were mixed with blood and luciferin and then incubated for one hour before imaging. Approximately 1000 cells could be detected above the background level of the blood alone. The signal emitted from the highest number of cells tested ($1.25\times10^6$) was approximately 2000 times greater than blood alone. The BL signal correlated strongly with cell number. FIG. 9C shows that the number of HL-60luc cells shows a linear correlation with BL.

Sensitivity of HL-60luc Cells to a Bacterial Toxin.

Figure 10A:
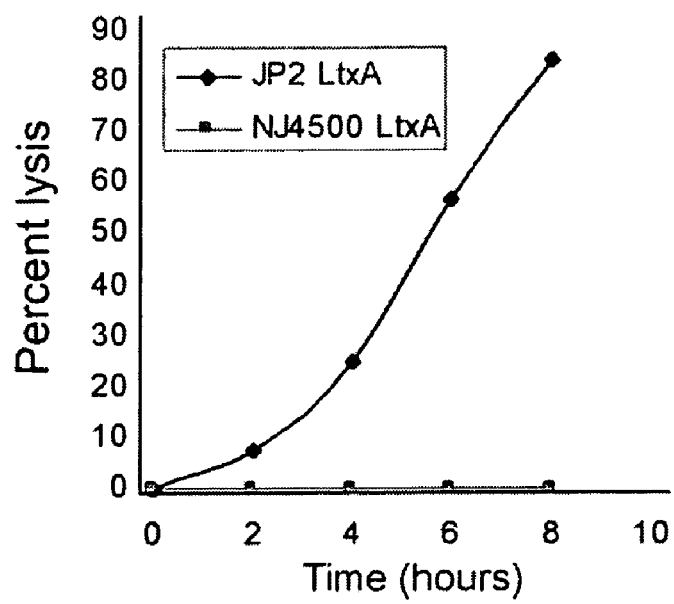
FIG. 10 shows effects of LtxA on cells. (A) Lysis of human red blood cells by LtxA from two different strains of *A. actinomycetemcomitans*. (B) HL-60 and HL-60luc cells are equally sensitive to killing by LtxA from strain NJ4500. Assays were performed in RPMI medium and viability was determined using the trypan blue dye exclusion assay.

The gram negative bacterium, *A. actinomycetemcomitans*, produces leukotoxin (LtxA), a protein toxin that kills specifically white blood cells from humans and Old World Primates (37-39) and red blood cells (1). Examination of LtxA from a strain of *A. actinomycetemcomitans*, NJ4500, revealed that this purified protein does not lyse erythrocytes in vitro compared to LtxA from the standard strain, JP2. FIG. 10A shows the lysis of human red blood cells by LtxA from two different strains of *A. actinomycetemcomitans*. Because erythrocyte lysis would be an undesirable property for a chemotherapeutic agent, studies here employ LtxA from NJ4500.

Figure 10B:
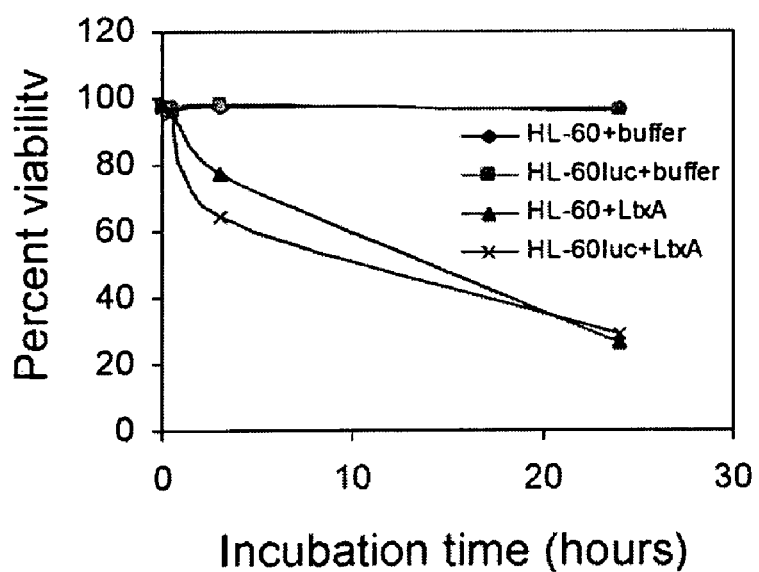

To determine if HL-60luc cells are equally sensitive to LtxA as parental HL-60 cells, cell killing was assayed by LtxA in RPMI. HL-60 cells were mixed with LtxA and viability was measured with the trypan blue dye exclusion assay using the Vi-CELL instrument. LtxA had an equal toxic effect on both cell lines. FIG. 10B shows that HL-60 and HL-60luc cells are equally sensitive to killing by LtxA from strain NJ4500. Assays were performed in RPMI medium and viability was determined using the trypan blue dye exclusion assay. This result was highly reproducible. Thus, the HL-60luc cell line is similar to the parental HL-60 cell line for it sensitivity to a bacterial toxin.

LtxA Activity in Whole Blood.

Figure 11A:
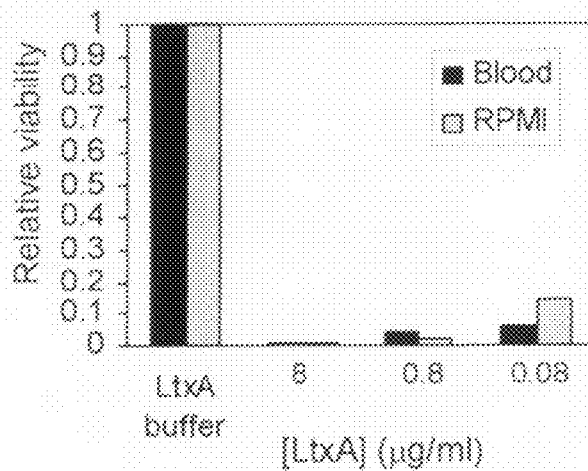
FIGS. 11A-11C show the cytotoxicity of LtxA and chlorambucil. (A) Activity of LtxA against HL60luc cells in whole human blood and RPMI medium. Viability was measured using BL. (B) Comparison between BL and trypan blue as viability assays for LtxA-mediated cytotoxicity. Cells were incubated in RPMI medium with LtxA or buffer for 4 hours and viability was determined. (C) Comparison between BL and trypan blue as viability assays for chlorambucil-mediated cytotoxicity. Cells were incubated in RPMI medium with chlorambucil or buffer for 24 hours and viability was determined

To determine if LtxA is active in whole blood and retains its ability to kill HL-60 cells, HL-60luc cells were resuspended in blood or RPMI and different concentrations of purified LtxA or LtxA buffer was added to the HL-60luc-blood mixture and incubated at 37° C. for 4 hours. BLI was then measured and relative viabilities were determined comparing experimental values to the buffer-containing sample. LtxA was highly active in whole blood against HL-60luc cells and this activity was similar to that seen in RPMI. FIG. 11A shows the activity of LtxA against HL60luc cells in whole human blood and RPMI medium. Viability was Measured Using BL.

Figure 11B:
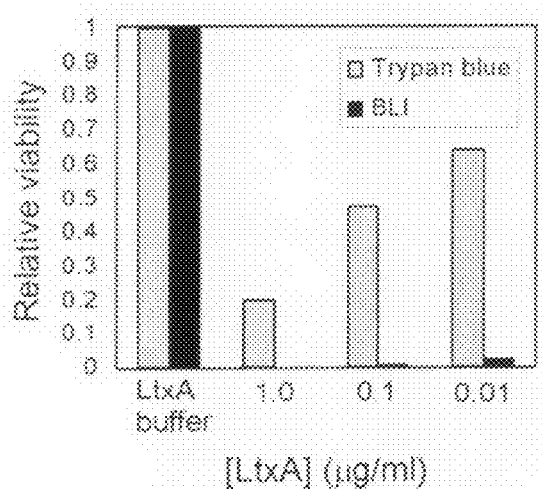

The sensitivity of BL to trypan blue as an assay for cell viability was also compared. Luminescence was significantly more sensitive than trypan blue. FIG. 11B shows the comparison between BL and trypan blue as viability assays for LtxA-mediated cytotoxicity. Cells were incubated in RPMI medium with LtxA or buffer for 4 hours and viability was determined. Nearly complete cell killing was observed with leukotoxin concentrations as low as 10 ng/ml using BL values. In contrast, trypan blue revealed that only 35% killing had occurred at this concentration.

Figure 11C:
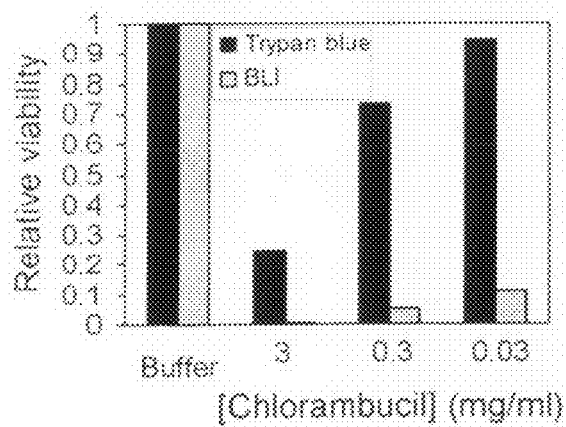

To determine if the difference in detection limit between the two methods was specific for LtxA-mediated cytotoxicity, another compound, chlorambucil, was used to induce cell death. Chlorambucil alkylates DNA and induces apoptosis (2,21) and therefore represents a mechanism of killing different from that of LtxA. For chlorambucil, it was also observed that BLI was a more sensitive assay than trypan blue for detecting viability. FIG. 4C shows the comparison between BL and trypan blue as viability assays for chlorambucil-mediated cytotoxicity. Cells were incubated in RPMI medium with chlorambucil or buffer for 24 hours and viability was determined. At a chlorambucil concentration of 0.03 mg/ml, BLI revealed approximately 90% cell death after 24 hours while trypan blue revealed essentially no killing (FIG. 11C).

Visualization of HL-60luc in Mice.

Mouse models for human leukemia utilize HL-60 cells that are injected either i.p. (28) or i.v. (40,41). To determine if the HL-60 luc cells could be visualized in living mice, approximately $10^6$ HL-60luc cells were injected i.p. or tail i.v. FIG. 12 shows Swiss-Webster mice that were anesthesized with XXX and injected with $10^6$ HL-60luc cells intraperitoneally (i.p.; top) or intravenously (i.v.; bottom) and followed by luciferin i.p. Mice were imaged with the IVIS 50 instrument at different times post-luciferin injection. The scale on the right of each image indicates surface radiance (photons/second/cm2/steradian). Luciferin was administered immediately following injection of cells and the animals were imaged with the IVIS 50 instrument. The cells could be detected with a 2-3 minute exposure when administered by either route. The signal was greatest for i.p.-injected cells immediately following injection while the signal for i.v.-injected cells peaked approximately 35 minutes post luciferin (FIG. 12). Interestingly, the signal observed for i.v. injection follows the path of the tail vein and then dissipates as the cells become diluted through other blood vessels. Thus, HL-60 cells can be visualized in a living animal at concentrations normally used for the SCID mouse model for human leukemia.

REFERENCES

1. Balashova, N. V., J. A. Crosby, L. Al Ghofaily and S. C. Kachlany. 2006. Leukotoxin confers beta-hemolytic activity to *Actinobacillus actinomycetemcomitans*. Infect Immun 74:2015-2021.
2. Begleiter, A., M. Mowat, L. G. Israels and J. B. Johnston. 1996. Chlorambucil in chronic lymphocytic leukemia: mechanism of action. Leuk Lymphoma 23:187-201.
3. Brandon, E. F., C. D. Raap, I. Meijerman, J. H. Beijnen and J. H. Schellens. 2003. An update on in vitro test methods in human hepatic drug biotransformation research: pros and cons. Toxicol Appl Pharmacol 189:233-246.
4. Clarke, J., W. Leach, S. Pippig, A. Joshi, B. Wu, R. House and J. Beyer. 2004. Evaluation of a surrogate antibody for preclinical safety testing of an antiCD11a monoclonal antibody. Regul Toxicol Pharmacol 40:219-226.
5. Contag, C. H. and M. H. Bachmann. 2002. Advances in in vivo bioluminescence imaging of gene expression. Annu Rev Biomed Eng 4:235-260.
6. Cooper, L. J., Z. Al-Kadhimi, L. M. Serrano, T. Pfeiffer, S. Olivares, A. Castro, W. C. Chang, S. Gonzalez, D. Smith, S. J. Forman and M. C. Jensen. 2005. Enhanced antilymphoma efficacy of CD19-redirected influenza MP1 specific CTLs by cotransfer of T cells modified to present influenza MP1. Blood 105:1622-1631.
7. Diaz, R., L. A. Ghofaily, J. Patel, N. V. Balashova, A. C. Freitas, I. Labib and S. C. Kachlany. 2006. Characterization of leukotoxin from a clinical strain of *Actinobacillus actinomycetemcomitans*. Microb Pathog 40:48-55.
8. Dumez, H., G. Guetens, G. De Boeck, M. S. Highley, E. A. de Bruijn, A. T. van Oosterom and R. A. Maes. 2005. In vitro partition of docetaxel and gemcitabine in human volunteer blood: the influence of concentration and gender. Anticancer Drugs 16:885-891.
9. Dumez, H., W. H. Reinhart, G. Guetens and E. A. de Bruijn. 2004. Human red blood cells: rheological aspects, uptake, and release of cytotoxic drugs. Crit Rev Clin Lab Sci 41:159-188.
10. Duvic, M., T. M. Kuzel, E. A. Olsen, A. G. Martin, F. M. Foss, Y. H. Kim, P. W. Heald, P. Bacha, J. Nichols and A. Liepa. 2002. Quality-of-life improvements in cutaneous T-cell lymphoma patients treated with denileukin diftitox (ONTAK). Clin Lymphoma 2:222-228.
11. Edinger, M., Y. A. Cao, Y. S. Hornig, D. E. Jenkins, M. R. Vemeris, M. H. Bachmann, R. S. Negrin and C. H. Contag. 2002. Advancing animal models of neoplasia through in vivo bioluminescence imaging. Eur J Cancer 38:2128-2136.
12. Fine, D. H., D. Furgang, H. C. Schreiner, P. Goncharoff, J. Charlesworth, G. Ghazwan, P. Fitzgerald-Bocarsly and D. H. Figurski. 1999. Phenotypic variation in *Actinobacillus actinomycetemcomitans* during laboratory growth: implications for virulence. Microbiology 145 (Pt 6):1335-1347.
13. Gallagher, R., S. Collins, J. Trujillo, K. McCredie, M. Ahearn, S. Tsai, R. Metzgar, G. Aulakh, R. Ting, F. Ruscetti and R. Gallo. 1979. Characterization of the continuous, differentiating myeloid cell line (HL-60) from a patient with acute promyelocytic leukemia. Blood 54:713-733.
14. Hill, P. J., G. S. Stewart and P. E. Stanley. 1993. Bioluminescence and chemiluminescence literature. Luciferase reporter genes--lux and luc. Part 2. J Biolumin Chemilumin 8:267-291.
15. Hollingshead, M. G., C. A. Bonomi, S. D. Borgel, J. P. Carter, R. Shoemaker, G. Melillo and E. A. Sausville. 2004. A potential role for imaging technology in anticancer efficacy evaluations. Eur J Cancer 40:890-898.
16. Jain, K. K. 2001. Use of bacteria as anticancer agents. Expert Opin Biol Ther 1:291-300.
17. Kuzmits, R., H. Rumpold, M. M. Muller and G. Schopf. 1986. The use of bioluminescence to evaluate the influence of chemotherapeutic drugs on ATP-levels of malignant cell lines. J Clin Chem Clin Biochem 24:293-298.
18. Lally, E. T., R. B. Hill, I. R. Kieba and J. Korostoff. 1999. The interaction between RTX toxins and target cells. Trends Microbiol 7:356-361.
19. Lally, E. T., I. R. Kieba, A. Sato, C. L. Green, J. Rosenbloom, J. Korostoff, J. F. Wang, B. J. Shenker, S. Ortlepp, M. K. Robinson and P. C. Billings. 1997. RTX toxins recognize a beta2 integrin on the surface of human target cells. J Biol Chem 272:30463-30469.
20. Liu, T. F., J. O. Urieto, J. E. Moore, M. S. Miller, A. C. Lowe, A. Thorburn and A. E. Frankel. 2004. Diphtheria toxin fused to variant interleukin-3 provides enhanced binding to the interleukin-3 receptor and more potent leukemia cell cytotoxicity. Exp Hematol 32:277-281.
21. Masta, A., P. J. Gray and D. R. Phillips. 1995. Nitrogen mustard inhibits transcription and translation in a cell free system. Nucleic Acids Res 23:3508-3515.
22. Mitsiades, C. S., N. S. Mitsiades, C. J. McMullan, V. Poulaki, R. Shringarpure, M. Akiyama, T. Hideshima, D. Chauhan, M. Joseph, T. A. Libermann, C. Garcia-Echeverria, M. A. Pearson, F. Hofmann, K. C. Anderson and A. L. Kung. 2004. Inhibition of the insulin-like growth factor receptor-1 tyrosine kinase activity as a therapeutic strategy for multiple myeloma, other hematologic malignancies, and solid tumors. Cancer Cell 5:221-230.
23. Mocanu, J. D., E. H. Moriyama, M. C. Chia, J. H. Li, K. W. Yip, D. P. Huang, C. Bastianutto, B. C. Wilson and F. F. Liu. 2004. Combined in vivo bioluminescence and fluorescence imaging for cancer gene therapy. Mol Imaging 3:352-355.
24. Nogawa, M., T. Yuasa, S. Kimura, J. Kuroda, K. Sato, H. Segawa, A. Yokota and T. Maekawa. 2005. Monitoring luciferase-labeled cancer cell growth and metastasis in different in vivo models. Cancer Lett 217:243-253.
25. Nyati, M. K., Z. Symon, E. Kievit, K. J. Dornfeld, S. D. Rynkiewicz, B. D. Ross, A. Rehemtulla and T. S. Lawrence. 2002. The potential of 5-fluorocytosine/cytosine deaminase enzyme prodrug gene therapy in an intrahepatic colon cancer model. Gene Ther 9:844-849.
26. Olsen, E., M. Duvic, A. Frankel, Y. Kim, A. Martin, E. Vonderheid, B. Jegasothy, G. Wood, M. Gordon, P. Heald, A. Oseroff, L. Pinter-Brown, G. Bowen, T. Kuzel, D. Fivenson, F. Foss, M. Glode, A. Molina, E. Knobler, S. Stewart, K. Cooper, S. Stevens, F. Craig, J. Reuben, P. Bacha and J. Nichols. 2001. Pivotal phase III trial of two dose levels of denileukin diftitox for the treatment of cutaneous T-cell lymphoma. J Clin Oncol 19:376-388.
27. Pereira, C., J. Damen, A. Eaves and E. Clarke. 2004. Toxicity testing: What bone marrow can tell us. BioProcess International 2:70-75.
28. Perentesis, J. P., R. Gunther, B. Waurzyniak, Y. Yanishevski, D. E. Myers, O. Ek, Y. Messinger, Y. Shao, L. M. Chelstrom, E. Schneider, W. E. Evans and F. M. Uckun. 1997. In vivo biotherapy of HL-60 myeloid leukemia with a genetically engineered recombinant fusion toxin directed against the human granulocyte macrophage colony-stimulating factor receptor. Clin Cancer Res 3:2217-2227.
29. Pessina, A., I. Malerba and L. Gribaldo. 2005. Hematotoxicity testing by cell clonogenic assay in drug development and preclinical trials. Curr Pharm Des 11:1055-1065.
30. Petty, R. D., L. A. Sutherland, E. M. Hunter and I. A. Cree. 1995. Comparison of MTT and ATP-based assays for the measurement of viable cell number. J Biolumin Chemilumin 10:29-34.
31. Rehemtulla, A., L. D. Stegman, S. J. Cardozo, S. Gupta, D. E. Hall, C. H. Contag and B. D. Ross. 2000. Rapid and quantitative assessment of cancer treatment response using in vivo bioluminescence imaging. Neoplasia 2:491-495.
32. Rocchetta, H. L., C. J. Boylan, J. W. Foley, P. W. Iversen, D. L. LeTourneau, C. L. McMillian, P. R. Contag, D. E. Jenkins and T. R. Parr, Jr. 2001. Validation of a noninvasive, real-time imaging technology using bioluminescent *Escherichia coli* in the neutropenic mouse thigh model of infection. Antimicrob Agents Chemother 45:129-137.
33. Sadikot, R. T., L. J. Wudel, D. E. Jansen, J. P. Debelak, F. E. Yull, J. W. Christman, T. S. Blackwell and W. C. Chapman. 2002. Hepatic cryoablationinduced multisystem injury: bioluminescent detection of NF-kappaB activation in a transgenic mouse model. J Gastrointest Surg 6:264-270.
34. Samson, D. J., J. Seidenfeld, K. Ziegler and N. Aronson. 2004. Chemotherapy sensitivity and resistance assays: a systematic review. J Clin Oncol 22:3618-3630.
35. Sarraf-Yazdi, S., J. Mi, M. W. Dewhirst and B. M. Clary. 2004. Use of in vivo bioluminescence imaging to predict hepatic tumor burden in mice. J Surg Res 120:249-255.
36. Sweeney, T. J., V. Mailander, A. A. Tucker, A. B. Olomu, W. Zhang, Y. Cao, R. S. Negrin and C. H. Contag. 1999. Visualizing the kinetics of tumor-cell clearance in living animals. Proc Natl Acad Sci USA 96:12044-12049.
37. Taichman, N. S., R. T. Dean and C. J. Sanderson. 1980. Biochemical and morphological characterization of the killing of human monocytes by a leukotoxin derived from *Actinobacillus actinomycetemcomitans*. Infect Immun 28:258-268.
38. Taichman, N. S., D. L. Simpson, S. Sakurada, M. Cranfield, J. DiRienzo and J. Slots. 1987. Comparative studies on the biology of *Actinobacillus actinomycetemcomitans* leukotoxin in primates. Oral Microbiol Immunol 2:97-104.
39. Taichman, N. S. and J. M. Wilton. 1981. Leukotoxicity of an extract from *Actinobacillus actinomycetemcomitans* for human gingival polymorphonuclear leukocytes. Inflammation 5:1-12.
40. Tomkinson, B., R. Bendele, F. J. Giles, E. Brown, A. Gray, K. Hart, J. D. LeRay, D. Meyer, M. Pelanne and D. L. Emerson. 2003. OSI-211, a novel liposomal topoisomerase I inhibitor, is active in SCID mouse models of human AML and ALL. Leuk Res 27:1039-1050.
41. Uckun, F. M. 1996. Severe combined immunodeficient mouse models of human leukemia. Blood 88:1135-1146.
42. Ugurel, S., D. Schadendorf, C. Pfohler, K. Neuber, A. Thoelke, J. Ulrich, A. Hauschild, K. Spieth, M. Kaatz, W. Rittgen, S. Delorme, W. Tilgen and U. Reinhold. 2006. In vitro drug sensitivity predicts response and survival after individualized sensitivity-directed chemotherapy in metastatic melanoma: a multicenter phase II trial of the Dermatologic Cooperative Oncology Group. Clin Cancer Res 12:5454-5463.
43. Vaidyanathan, S. and M. Boroujerdi. 2000. Interaction of dexrazoxane with red blood cells and hemoglobin alters pharmacokinetics of doxorubicin. Cancer Chemother Pharmacol 46:93-100.
44. Walensky, L. D., A. L. Kung, I. Escher, T. J. Malia, S. Barbuto, R. D. Wright, G. Wagner, G. L. Verdine and S. J. Korsmeyer. 2004. Activation of apoptosis in vivo by a hydrocarbon-stapled BH3 helix. Science 305:1466-1470.
45. Ward, T. H., S. Danson, A. T. McGown, M. Ranson, N. A. Coe, G. C. Jayson, J. Cummings, R. H. Hargreaves and J. Butler. 2005. Preclinical evaluation of the pharmacodynamic properties of 2,5-diaziridinyl-3-hydroxymethyl-6-methyl-1,4-benzoquinone. Clin Cancer Res 11:2695-2701.

All publications, including but not limited to patents and patent applications, cited in this specification are herein incorporated by reference as if each individual publication were specifically and individually indicated to be incorporated by reference herein as though fully set forth.

While preferred embodiments of the invention have been shown and described herein, it will be understood that such embodiments are provided by way of example only. Numerous variations, changes and substitutions will occur to those skilled in the art without departing from the spirit of the invention. Accordingly, it is intended that the appended claims cover all such variations as fall within the spirit and scope of the invention.

What is claimed is:

1. A method for treating leukemia comprising administering a composition comprising a leukotoxin protein isolated from the NJ4500 strain of *Actinobacillus actinomycetemcomitans* to a subject suffering from said leukemia.

2. The method of claim 1, wherein the composition is a pharmaceutical composition and comprises a pharmaceutically acceptable carrier.

3. The method of claim 1, wherein the leukemia is acute myeloid leukemia or chronic myeloid leukemia.

* * * * *